(12) United States Patent
O'Malley et al.

(10) Patent No.: US 9,419,520 B2
(45) Date of Patent: *Aug. 16, 2016

(54) BATTERY COMPENSATION SYSTEM USING PWM

(71) Applicant: ABOMINABLE LABS, LLC, Lake Oswego, OR (US)

(72) Inventors: Vincent O'Malley, Portland, OR (US); Jack Cornelius, Lake Oswego, OR (US)

(73) Assignee: ABOMINABLE LABS, LLC, Lake Oswego, OR (US)

( * ) Notice: Subject to any disclaimer, the term of this patent is extended or adjusted under 35 U.S.C. 154(b) by 515 days.

This patent is subject to a terminal disclaimer.

(21) Appl. No.: 14/046,969

(22) Filed: Oct. 6, 2013

(65) Prior Publication Data

US 2014/0033409 A1 Feb. 6, 2014

Related U.S. Application Data

(63) Continuation-in-part of application No. 13/397,691, filed on Feb. 16, 2012, now Pat. No. 8,566,962.

(51) Int. Cl.

| | |
|---|---|
| *H02M 3/156* | (2006.01) |
| *A61F 9/02* | (2006.01) |
| *G02B 27/00* | (2006.01) |
| *A61F 9/04* | (2006.01) |
| *A42B 3/24* | (2006.01) |
| *G02C 11/08* | (2006.01) |
| *B63C 11/12* | (2006.01) |
| *B63C 11/28* | (2006.01) |

(52) U.S. Cl.
CPC .............. *H02M 3/1563* (2013.01); *A42B 3/245* (2013.01); *A61F 9/025* (2013.01); *A61F 9/04* (2013.01); *G02B 27/0006* (2013.01); *G02C 11/08* (2013.01); *A61F 9/022* (2013.01); *A61F 9/028* (2013.01); *B63C 11/12* (2013.01); *B63C 11/28* (2013.01); *Y10T 307/422* (2015.04)

(58) Field of Classification Search
CPC ............ A61F 9/04; A42B 3/228; G02C 7/16; G02C 11/08; H05B 2203/036; G02B 7/1815
USPC ................ 2/15, 425, 426, 6.3, 427, 432, 435; 219/203, 211; 351/62; 359/512
See application file for complete search history.

(56) References Cited

U.S. PATENT DOCUMENTS

| | | | | |
|---|---|---|---|---|
| 3,160,735 | A | * 12/1964 | Aufricht ................ | G02C 11/08 2/435 |
| 4,027,231 | A | * 5/1977 | Lohrmann ............. | G01R 15/04 320/136 |
| 4,584,721 | A | 4/1986 | Yamamoto | |

(Continued)

*Primary Examiner* — Tejash Patel
(74) *Attorney, Agent, or Firm* — Howard Russell

(57) ABSTRACT

Compensation system adapted for use with a battery-powered, PWM-driven portable electronic device to enable consistent power to the device load despite battery voltage drop resulting from battery depletion, comprising: a voltage divider circuit for proportionally adjusting the voltage to a measurable range; an analog-to-digital converter for receiving the output from the voltage divider and converting it into a digital voltage value; and a microprocessing unit for running software code steps for receiving digital voltage input and user-determined power setting input for determining a compensating duty cycle for application by the software to the PWM to drive the load consistently at the user-determined power setting despite decrease in battery voltage resulting from battery depletion.

17 Claims, 17 Drawing Sheets

(56) References Cited

U.S. PATENT DOCUMENTS

| | | | |
|---|---|---|---|
| 4,868,929 A | 9/1989 | Curcio | |
| 4,942,629 A | 7/1990 | Stadlmann | |
| 5,105,067 A | 4/1992 | Brekkestran et al. | |
| 5,319,397 A * | 6/1994 | Ryden | G02C 11/08 219/211 |
| 5,351,339 A | 10/1994 | Reuber et al. | |
| 5,363,153 A * | 11/1994 | Bailiff | G02C 11/00 219/201 |
| 5,471,036 A * | 11/1995 | Sperbeck | H05B 3/36 2/435 |
| 5,778,689 A | 7/1998 | Beatenbough | |
| 6,040,660 A * | 3/2000 | Schmidt | H05B 39/044 315/136 |
| 6,470,696 B1 | 10/2002 | Palfy et al. | |
| 6,704,944 B2 | 3/2004 | Kawainshi et al. | |
| 6,896,366 B2 | 5/2005 | Rice et al. | |
| 6,927,368 B2 | 8/2005 | Cao et al. | |
| 7,387,022 B1 | 6/2008 | Korniyenko et al. | |
| 7,648,234 B2 | 1/2010 | Welchel et al. | |
| 8,566,962 B2 * | 10/2013 | Cornelius | A42B 3/245 2/15 |
| 2003/0091089 A1 | 5/2003 | Krausse | |
| 2003/0234778 A1 | 12/2003 | Kim | |
| 2004/0021444 A1 | 2/2004 | Peschke | |
| 2004/0050072 A1 | 3/2004 | Palfy et al. | |
| 2004/0050076 A1 | 3/2004 | Palfy et al. | |
| 2006/0289458 A1 | 12/2006 | Kim et al. | |
| 2008/0290081 A1 | 11/2008 | Biddell | |
| 2010/0087778 A1 | 4/2010 | Genosar et al. | |
| 2010/0141185 A1 | 6/2010 | Benning et al. | |
| 2011/0133655 A1 | 6/2011 | Recker et al. | |
| 2012/0194141 A1 | 8/2012 | Shi et al. | |

* cited by examiner

| Watts | 2.0 | 4.0 | 6.0 | 8.0 | 10.0 |
|---|---|---|---|---|---|
| Voltage | | Duty Cycle | | | |
| 8.4 | 11.3 | 22.7 | 34.0 | 45.4 | 56.7 |
| 8.3 | 11.6 | 23.2 | 34.8 | 46.5 | 58.1 |
| 8.2 | 11.9 | 23.8 | 35.7 | 47.6 | 59.5 |
| 8.1 | 12.2 | 24.4 | 36.6 | 48.8 | 61.0 |
| 8.0 | 12.5 | 25.0 | 37.5 | 50.0 | 62.5 |
| 7.9 | 12.8 | 25.6 | 38.5 | 51.3 | 64.1 |
| 7.8 | 13.1 | 26.3 | 39.4 | 52.6 | 65.7 |
| 7.7 | 13.5 | 27.0 | 40.5 | 54.0 | 67.5 |
| 7.6 | 13.9 | 27.7 | 41.6 | 55.4 | 69.3 |
| 7.5 | 14.2 | 28.4 | 42.7 | 56.9 | 71.1 |
| 7.4 | 14.6 | 29.2 | 43.8 | 58.4 | 73.0 |
| 7.3 | 15.0 | 30.0 | 45.0 | 60.0 | 75.1 |
| 7.2 | 15.4 | 30.9 | 46.3 | 61.7 | 77.2 |
| 7.1 | 15.9 | 31.7 | 47.6 | 63.5 | 79.3 |
| 7.0 | 16.3 | 32.7 | 49.0 | 65.3 | 81.6 |
| 6.9 | 16.8 | 33.6 | 50.4 | 67.2 | 84.0 |
| 6.8 | 17.3 | 34.6 | 51.9 | 69.2 | 86.5 |

| Watts | | | | | | |
|---|---|---|---|---|---|---|
| Voltage | 1.5 | 3.0 | 4.5 | 6.0 | 7.5 | |
| | | | Duty Cycle | | | |
| 8.4 | 8.5 | 17.0 | 25.5 | 34.0 | 42.5 | |
| 8.3 | 8.7 | 17.4 | 26.1 | 34.8 | 43.5 | |
| 8.2 | 8.9 | 17.8 | 26.8 | 35.7 | 44.6 | |
| 8.1 | 9.1 | 18.3 | 27.4 | 36.6 | 45.7 | |
| 8.0 | 9.4 | 18.8 | 28.1 | 37.5 | 46.9 | |
| 7.9 | 9.6 | 19.2 | 28.8 | 38.5 | 48.1 | |
| 7.8 | 9.9 | 19.7 | 29.6 | 39.4 | 49.3 | |
| 7.7 | 10.1 | 20.2 | 30.4 | 40.5 | 50.6 | |
| 7.6 | 10.4 | 20.8 | 31.2 | 41.6 | 51.9 | |
| 7.5 | 10.7 | 21.3 | 32.0 | 42.7 | 53.3 | |
| 7.4 | 11.0 | 21.9 | 32.9 | 43.8 | 54.8 | |
| 7.3 | 11.3 | 22.5 | 33.8 | 45.0 | 56.3 | |
| 7.2 | 11.6 | 23.1 | 34.7 | 46.3 | 57.9 | |
| 7.1 | 11.9 | 23.8 | 35.7 | 47.6 | 59.5 | |
| 7.0 | 12.2 | 24.5 | 36.7 | 49.0 | 61.2 | |
| 6.9 | 12.6 | 25.2 | 37.8 | 50.4 | 63.0 | |
| 6.8 | 13.0 | 26.0 | 38.9 | 51.9 | 64.9 | |

Fig. 17

BATTERY COMPENSATION SYSTEM USING PWM

CROSS-REFERENCE TO AND INCORPORATION BY REFERENCE OF RELATED APPLICATION

This application is a continuation-in-part of prior co-pending U.S. patent application Ser. No. 13/397,691 filed Feb. 16, 2012 for PWM Heating System for Eye Shield, Publication No. US-2013-0212765-A1, Published Aug. 22, 2013 (hereafter also referred to as "the Parent Application"). This application claims the benefit of the priority date of the Parent Application and applicant hereby disclaims any terminal period of any patent issuing on the present application that extends beyond 20 years from the priority date of any patent issuing on the Parent Application. The Parent Application is hereby incorporated by reference in this application.

FIELD OF INVENTION

This invention relates to regulating power from a battery to drive a load, and more particularly to compensating for a decrease in voltage from a Lithium-Ion battery as it dissipates over time in use to consistently power a portable electronic device.

BACKGROUND OF THE INVENTION

Various products, from anti-fog sport goggles, dive masks and other highly portable transparent anti-fog eye-protecting shields, to hand-held GPS devices, radios, telephones and other portable electronics devices having display units, use batteries not only to power these devices but also to heat the devices to prevent fogging of an eye shield or viewing screen. And while some of these devices have commonly used Lithium-Ion batteries to power the devices, the use of Lithium-Ion batteries is not as well known in others, such as the powering of heated eye shields. And yet it would seem desirable to use the benefits of Lithium-Ion battery technology in many more such devices to provide power to provide power to them them, except that a known issue with Lithium-Ion batteries is the fact that, as their charge decreases over time in use, the voltage output they provide also decreases over time in use.

A common characteristic of such portable devices is the fact that they are light weight enough to be carried on a user's body, e.g., worn on a user's head. Examples of fog-prone sport goggles intended for use during winter activities, have included goggles for downhill skiing, cross-country skiing, snowboarding, snowmobiling, sledding, tubing, ice climbing and the like, and are widely known and widely utilized by sports enthusiasts and others whose duties or activities require them to be outside in snowy and other inclement cold weather conditions. Examples of fog-prone dive masks have included eye and nose masks independent of a breathing apparatus as well as full-face masks in which the breathing apparatus is integrated into the mask. Examples of fog-prone eye-protecting shields have included a face shield that a doctor or dentist would wear to prevent pathogens from getting into the user's mouth or eyes, or a transparent face shield portion of a motorcycle helmet. Fogging that impairs vision is a common problem with such goggles, dive masks and eye-protecting shields.

Examples of hand-held devices that require consistent power to heat the displays of such devices to prevent fogging of the display have included hand-held GPS units, radios, telephones, medical devices (EKG readouts), readers, tablets, portable computers, point of sale terminals, etc.

There have been various conductive apparatus devised for preventing condensation build-up on eye-shields and viewing screens of such hand-held devices. The purpose of these conductive apparatus has been to provide an eye shield and viewing screen that may be maintained free of condensation so that the user would be able to enjoy unobstructed vision and viewing during viewing activities. Prior sports goggles and hand-held electronic devices with electronic systems have been primarily used in environments requiring a high degree of portability, that is, where a power source for powering the electronics for the device has been advantageously carried on a strap for the goggle or on the device itself as shown and described in co-pending U.S. Patent Application Ser. No. 61/563,738, by McCulloch, for Modular Anti-fog Goggle System. While such battery-powered devices, especially heating devices which consume extraordinary amounts of power from batteries, need to be judicious in the use of total power source, generally measured in amp-hours, to preserve power source life, it has also become important that the power circuitry of such systems provide a consistent level of power to the device, even though the device battery may become increasingly depleted over time in use. Thus, the ability to adjust the amount of current delivered to the device's resistive element, compensated for decreasing voltage as the battery charge is depleted, has also become desirable.

Thus, while it has remained an important goal to maximize battery life, in which case the use of pulse-width modulation (PWM) has proven useful as described in co-pending U.S. patent application Ser. No. 13/397,691 for PWM Heating System for Eye Shield, Publication No. US-2013-0212765-A1, the limitation of Lithium-Ion battery depletion and correspondent voltage depletion has remained a problem. Thus, it has been recognized that, where there is sufficiently available battery power to perform heating operations on a goggle or hand-held device, an appropriate amount of additionally available power may be useful to make power supplied to the device more consistent throughout the depletion cycle of the battery.

No prior art goggle or hand-held electronic devices have made use of their battery supplies to provide consistent power to the device despite depletion of battery charge. U.S. Pat. No. 4,868,929, to Curcio, for Electrically Heated Ski Goggles, comprises an eye shield with embedded resistive wires operatively connected via a switching device to an external power source pack adapted to produce heating of the eye shield for anti-fog purposes. U.S. Pat. No. 7,648,234, to Welchel et al., for Eyewear With Heating Elements, discloses use of nichrome and thin film heating elements used for heating an eye shield and discloses use of a control mechanism for turning on and off the heat to the eye shield. Neither discusses the foregoing power regulation, conservation and distribution concepts using PWM circuitry to provide more even power to the device despite charge depletion.

A problem with sport goggles which have employed electrical heating is that of uneven heating over the entire surface of the eye shield. Goggles and goggle eye-shields are manufactured with an irregular shape required to maintain a position close to the face of the wearer and allowing cutouts for the nose and extended edges for peripheral vision. Even heating of this irregular shape has not been accomplished in the prior art.

Prior art devices having irregularly-shaped eye shields have been susceptible to hot spots, and using such devices in limited battery-powered applications has unduly discharged the battery. The reason for the hot spots has been because the electrical resistivity between the electrical connections across the resistive elements on the eye shield has been greater or lesser at different locations on the eye shield such that the amount of electrical current consumed in the areas with less distance between terminal connections is greater and the amount of electrical current consumed in areas with greater distance between the terminal connections is less. For example, where the terminals are on either side of the lens in a resistive wiring application, there have been problems with evenly heating the lens since the distance the wire has had to travel from one terminal to the other has been greater for those wires traveling over the bridge of the nose and down under the eyes than other wires that travel the shorter distance across a central portion of the lens. To overcome fogging conditions enough power must be applied to overcome the fog in the areas with the greatest distance between the terminal connection points, causing the smaller areas to overheat, which in turn wastes power. Thus, the problem has resulted in limited usefulness of heating of goggle eye-shields. Because of the irregular shape of eye shields, these problems exist whether one is considering resistive wire applications or resistive-film applications.

Thus there has developed a need to provide a preferably automatically adjusting variable power source which can provide adequate current to meet the requirements of anti-fogging a device, or heating of the device for other reasons, all while providing consistent power despite battery depletion across the load and without presenting excessive power above that which is required. Also there has developed a need to provide multiple current supplies to multiple heating element regions to enable even heating of goggle eye-shields across the entire eye shield surface while providing consistent power despite battery depletion across each region, or load, but without excessive use of power or hot-spots at each region, or load.

Switching the power on to a goggle when you experience fog conditions, and then switching it off when a user suspects it is no longer needed, or doing this to otherwise provide desired heat or power to a hand-held device, is not an efficient way to overcome fog or to otherwise heat or provide power to a device. This is because while the device is on, it is using full power and this is an inefficient use of battery resources. Also, the user doesn't really know precisely when to turn it off, so at best the user is guessing when is the best time to turn it off. Further, when a user is involved and concentrating on the activity at hand, it often is not convenient to have to turn on, or off, the power to heat the eye shield or other hand-held device. Manual switching of power to an eye shield or other hand-held device doesn't allow the user to set an intermediate heat value that is sufficient to curtail fogging or otherwise heat but which also conserves battery life. Further, there are no known systems disclosed in the prior art for balanced heating of a film or other resistive element on an eye shield or hand-held screen, while compensating to provide consistent power despite battery depletion, which also provide variable control of a heating element on the device.

SUMMARY OF THE INVENTION

In accordance with an aspect of the invention, there is provided an eye-shield condensation preventing system comprising: an eye shield adapted for protecting a user's eyes and adapted for defining at least a partially enclosed space between the user's eyes and the eye shield, a power source, a pulse-width modulator (PWM), a switching means responsive to the pulse-width modulator, a heating element on the eye shield, and a circuit interconnecting the power source, the pulse-width modulator, the switching means and the heating element for controlling heating of the eye shield. Preferably, the switching means comprises a metal-oxide-semiconductor field-effect transistor.

The device of this aspect of the invention provides a single-PWM, single heating region eye shield fog prevention device that enables efficient heating of the eye shield or lens so that battery life is maximized, since PWM can be preset to an output having a percentage ratio of on to off cycles that is tailored specifically to the particular goggle lens to which power is being applied.

In accordance with another aspect of the invention, there is provided an eye-shield condensation preventing system comprising: an irregular-shaped eye shield comprising a surface area divisible into a plurality of regions of one or more sizes to facilitate divisible heating of the eye-shield, the eye shield being adapted for protecting a user's eyes and adapted for defining at least a partially enclosed space between the user's eyes and the shield. The system further comprises a power source, a plurality of PWMs, each PWM operatively connected with the power source and a plurality of switching means, each switching means responsive to a corresponding PWM. With this aspect of the invention, there are a plurality of heating elements on the eye-shield, each the heating element extending to a corresponding size region of the eye-shield, and a plurality of circuits, each the circuit interconnecting one of the PWMs with a corresponding one of the switching means and one of the corresponding heating elements. Each the PWM produces a duty cycle for providing an amount of current to the corresponding heating element such that the power output of each region of the eye shield corresponds to a desired output for the region of the eye shield.

In accordance with the aspects of the invention described above, there is provided an eye-shield condensation preventing system comprising: an eye-shield adapted for protecting a user's eyes and adapted for defining at least a partially enclosed space between the user's eyes and the eye shield, the eye shield having a surface area divisible into at least one region for facilitating region heating of the eye-shield to a desired temperature, a power source, at least one PWM, at least one heating element on and corresponding with the at least one region for facilitating region heating of the eye shield, the at least one heating element corresponding with the at least one PWM. In this embodiment, there is at least one circuit interconnecting the power source, the at least one PWM and the at least one corresponding heating element for heating the eye shield, wherein the at least one PWM controls current to maintain the temperature of the at least one heating element region to a temperature above the anticipated dew point of an operating environment.

The device of the multiple-region aspect of the invention provides a multiple-PWM resistive film heating system on the eye shield or lens surface that is divided into multiple regions, for example regions according to irregular and differently-shaped portions of the lens such as directly over the bridge of the nose as compared to directly in front of the eyes, to enable even heating of differently-shaped or sized regions. Thus, for example, the regions may be used to divide the lens into a plurality of regions, each of similar area from one region to the next, to enable more even heating across the eye shield. Or, conversely this division may be used to allow specific heating of a certain area of the eye shield, for example to ensure proper function of an electronic display portion of the lens.

In accordance with another aspect of the invention building on the multiple-region aspect of the invention, the PWMs may be operated in accordance with a profile such that the power per square unit, i.e., power density, of each region of the eye shield may be assured to be substantially equal and evenly distributed across the region regardless of the size of each region. Or, alternatively, heating of the regions may be independently adjusted to create a specific profile desired for a particular eye shield to account for various pre-determined weather conditions, various activities or eye shield types, shapes and sizes.

Preferably, the plurality of PWMs of this aspect of the invention comprises a microcomputer capable of simultaneously performing a plurality of various internal PWM functions corresponding to the plurality of PWMs, the microcomputer having a plurality of I/O ports for interconnecting the internal PWM functions with the plurality of circuits. Further, preferably, each of the switching means in accordance with this aspect of the invention comprises a metal-oxide-semiconductor field-effect transistor (MOSFET).

In accordance with another aspect of the invention, whether involving the single-region, single-PWM device, or whether involving the multiple-region, multiple-PWM device, there is provided an eye-shield condensation preventing system as previously summarized which further comprises a current adjustment means (CAM) operatively connected to each PWM (whether a single-PWM embodiment or a multiple PWM embodiment) for varying duty cycle of the power source via each PWM in turn varying the amount of current delivered to each heating element.

The device of this aspect of the invention provides the ability of the CAM for efficient managing of the temperature of the eye shield lens at a temperature that is just above the dew point temperature to effectively prevent fogging with a minimum of attention by the user. This, in turn, allows power savings to enable longer battery life.

In accordance with another aspect of the invention, there is provided an eye-shield condensation preventing system as previously described, whether a multiple-region, multiple-PWM embodiment, or a single-region, single-PWM embodiment, the device further comprising means for measuring ambient temperature and relative humidity and means for calculating dew point. The means for calculating dew point in this aspect of the invention is preferably operatively connected with the CAM (preferably further comprising microcomputer means) such that the CAM increases power to the electrical circuit when temperature within the space by the eye shield falls below the dew point temperature threshold and reduces power to the electrical circuit when temperature within the space defined by the eye shield climbs above the dew point temperature threshold. Thus the invention is capable of feeding a pulse to the resistive heating element, e.g., the film heating element, that is just enough to keep it at just above the dew point to effectively and automatically prevent fogging and to conserve battery life. The means for calculating dew point preferably comprises microcomputer means operatively connected with the temperature and relative humidity sensing means.

The eye-shield condensation preventing system of this aspect of the invention may further comprise a relative humidity sensor and a temperature sensor, each sensor located within the space defined by the eye shield. Such a system further comprises means, for example microcomputer means, operatively connected with the relative humidity and temperature sensor for periodically calculating dew point temperature. Further, the at least one pulse-width modulator is responsive to the means for periodically calculating dew point temperature to control the at least one heating element such that the at least one heating element is maintained at a temperature at above dew point to assure prevention of fogging over time.

In accordance with another aspect of the invention, the eye-shield condensation preventing system of the previous two aspects of the invention, as pertaining to multiple-region embodiments of the invention, may further comprise region profiling logic enabling a single adjustment from the variable current adjustment mechanism to affect proportional adjustments to each region relative to other regions. Thus, the invention provides varying coordinated duty cycles to power multiple resistive regions of an eye shield for the purpose of distributing heating evenly throughout the entire eye shield by adjusting the power delivered to each segment based on a profile of the eye shield. Further, the device of this aspect of the invention provides automated profile characteristics incorporated into the fog prevention system such that desired heating of the lens, whether it be even heating across multiple regions across the entire lens, or a pre-determined specific heating pattern, or heating footprint using different regions of the lens, may be maintained upon manual, or automated, adjustment of the heating power directed to the lens.

In accordance with yet another aspect of the invention, there is provided an eye-shield condensation preventing system as described above in the single-region or the multiple-region aspects of the invention as described above, and further in accordance with the previous aspect of the invention comprising a plurality of predetermined data profiles and corresponding selection means enabling control of each region of the eye shield in accordance with a user-selected one of the data profiles.

The device of this aspect of the invention provides selectable profile characteristics incorporated into the eye shield fog preventing system such that appropriate heating may be selected by the user depending upon weather and activity level conditions, or eye-shield features employed, such as video recording, heads-up display, global positioning system, etc.

Each of the eye shields disclosed herein are adapted for protecting a user's eyes from wind, debris, snow, rain, extreme temperatures and elements which could harm the eyes or otherwise impair vision. Each eye shield is also adapted to form and define at least a partial enclosure around and in front of the eyes. This enclosure warms up relative to conditions outside of the enclosure as a result of body heat transmitted into the space defined by the eye shield, and the enclosure also experiences higher relative humidity compared to outside conditions as a result of perspiration. When the temperature of the eye shield drops below the temperature within the eye shield at which dew, or condensation, would form on the inside of the eye shield, fogging of the eye shield occurs.

One purpose of the present invention is to provide an eye shield fog prevention system that effectively prevents the eye shield from fogging, regardless of weather conditions. Another purpose of the present invention is to provide an eye shield fog prevention system that employs PWM in such a way that power and energy are conserved and battery life is extended. Another purpose of the invention is to provide an eye shield fog prevention system that adjusts the power to the heater on the lens in accordance with current dew point conditions, either manually, or automatically, increases power to the eye shield as temperature within the eye shield is less than or falls below the dew point temperature, or so decreases power when temperature within the eye shield is above the dew point temperature. Another purpose of the present invention is to provide an eye shield fog preventing system that assures and simplifies the attainment of fog-free usage in varying weather and activity conditions, with a plurality of different sized and shaped eye shields, by providing profiles that at least partially automate heating of the eye-shield. Yet another purpose of the invention is to provide such profiles that are user selectable. The foregoing listing is not intended as an exclusive listing of purposes of the invention, there may be other purposes for which the invention may be suited which are not listed, and the presence or absence of any such purpose herein shall not necessarily limit the spirit and scopes of the invention as further defined and claimed herein.

The shield condensation preventing system of any of the foregoing aspects of the invention may be adapted for use for heating in an anti-fog sport goggle or any protective eye-shield, such as for skiing, inner-tubing, tobogganing, ice-climbing, snow-mobile riding, cycling, running, working with patients, in other medical or testing environments, and the like. Further, the system of any of the foregoing aspects of the invention may be adapted for use in a diving mask.

In accordance with another aspect of the invention, there is provided a compensation system adapted for use with any of the foregoing battery-powered, PWM-driven eye shields, or other portable electronic device, to enable consistent power to the device load despite battery voltage drop resulting from battery depletion. The compensation system in accordance with this aspect of the invention comprises: a voltage divider circuit for proportionally adjusting the voltage to a measurable range; an analog to digital converter for receiving the output from the voltage divider and converting it into a digital voltage value; and means for receiving digital voltage input and user-determined power setting input for determining a compensating duty cycle for application to the PWM to drive the load consistently at the user-determined power setting despite decrease in battery voltage resulting from battery depletion. Preferably, the voltage divider circuit of an embodiment in accordance with this aspect of the invention comprises two precision resistors in series between positive and negative terminals of the battery for proportionally adjusting the voltage to a measurable range, the voltage divider circuit preferably having a tap between the two resistors adapted to provide the proportional voltage measurement to an I/O pin on an analog-to-digital converter. Preferably, the user-determined, or provided, power setting for this and another aspect of the invention comprises a power level setting set by a dial, a knob, or a push button system, together with some form of visual feedback to the user to further enable selection of the setting.

In accordance with an embodiment of the invention, there may be provided mode switching means for user selection of battery conservation mode or consistent power output mode. The battery conservation mode provides an off switch for the compensation system, whereas the consistent power mode provides an on switch for the compensation system. Though the battery conservation mode uses less battery power than the consistent power mode, for those times where there is sufficient battery power to use the consistent power mode, it may be preferable to a user to do so, since a user-determined power level in this latter mode would yield results consistent with what a user would expect with an otherwise fully-charged battery. The selection of battery conservation mode or consistent power mode depends upon the total battery charge available, the longevity of a particular battery as experienced by the user, and the anticipated level of heating required for a number of use hours anticipated by the user.

In accordance with an embodiment of the invention, the battery compensation system is adapted for use with at least one lithium-ion battery-powered, PWM-driven portable electronic device. Such a portable device may include an anti-fog eye shield, such as for example a ski goggle, a diving mask, a motorcycle or snowmobile helmet visor, or a medical or testing visor. Or, alternatively, such a portable device may include a hand-held GPS unit, a hand-held radio, or a cell phone.

In accordance with an embodiment of the invention, the compensation system of the invention further comprises a metal-oxide-semiconductor field-effect transistor switching means responsive to the pulse-width modulator. Further, in accordance with an embodiment of the invention, the compensation system of the invention further comprises current adjustment means operatively connected to the pulse-width modulator for varying duty cycle of the power source via the pulse-width modulator in turn varying the mount of current delivered to the load.

In accordance with an embodiment of the invention, the means for receiving voltage input and user-determined power setting input for determining compensating duty cycle comprises a microprocessing unit for receiving voltage input and user-determined power setting input and executing software code to determine a compensating duty cycle for application by the software to the PWM to drive the load consistently at the user-determined power setting despite decrease in battery voltage resulting from battery depletion. For this embodiment of the invention, the microprocessing unit is preferably a battery-powered microprocessing unit. It will be appreciated by those of ordinary skill in the art that readily-available microprocessing units having on-board analog-to-digital conversion means may be used for the present invention.

Still further, determination of a compensating duty cycle may comprise a data lookup table of PWM duty cycle values organized according to power setting and battery depletion voltage drop and for use by the code steps run by the microprocessor to select a compensating duty cycle for application to the PWM to drive the load consistently at the user-determined power setting despite decrease in battery voltage resulting from battery depletion. This embodiment of the invention including a lookup table provides generally faster operation and is easier to code than using floating-point calculations, though it will be appreciated that either may be used to implement the invention in accordance with its true spirit and scope. Further, while conceivably a discrete logic circuit could be used to perform the functions of the compensation system of the invention, such would likely be unduly expensive to implement and no more effective than the software and data table lookup functions that are preferred for the invention.

In an alternate embodiment, the software steps themselves may be used to calculate a compensating duty cycle for application to the PWM to drive the load consistently at the user-determined power setting despite decrease in battery voltage resulting from battery depletion. The formula for determining the compensating duty cycle for this embodiment of the invention, which is the same formula used to determine data table duty cycle values (from user input power settings and measured voltage) used in a previous software embodiment is as follows:

$$\text{Duty Cycle} = \frac{\text{Desired Power} * \text{Load Resistance}}{(\text{Battery Voltage})^2} * 100$$

The compensation system in accordance with this aspect of the invention enables maintenance of a user-selected and/or desired power setting to drive a load to consistently heat a portable device, such as anti-fog goggles or a hand-held GPS, radio or phone, despite partial depletion of a device battery, as long as there is sufficient battery charge to maintain the system-compensated power output. Thus, as the voltage from the battery drops resulting from battery depletion from use over time, the system compensates by increasing the duty cycle of the PWM driver for the device.

In accordance with another aspect of the invention, there is provided an alternative embodiment compensation system adapted for use with a battery-powered, multi-channel PWM-driven portable electronic device having a plurality of loads corresponding to each PWM channel to enable consistent power to each of the loads of the device despite battery voltage drop resulting from battery depletion. The compensation system in accordance with this aspect of the invention comprises: a voltage divider circuit for proportionally adjusting the voltage to a measurable range; an analog to digital converter for receiving the output from the voltage divider and converting it into a digital voltage value; and a microprocessing unit for running software code steps for receiving digital voltage input and user-determined power setting input for each load for determining a compensating duty cycle for application by the software to each PWM channel to drive each corresponding load consistently at the user-determined power setting despite decrease in battery voltage resulting from battery depletion.

The compensation system in accordance with this aspect of the invention enables compensation for a depleting battery source for maintaining, with the use of a multi-channel PWM system, consistent power over time to each of a plurality of loads of a portable device (as long as there remains sufficient battery charge to power the device), such as a multi-region, anti-fog eye shield powered by the system to evenly heat each of the regions across the eye shield to a consistent temperature. Alternatively, such a system in accordance with this aspect of the invention may be used to provide consistent heating, despite battery depletion over time, to heat a multi-heating-element-region eye shield to prevent fogging in each of the regions according to a custom heating profile applied to the eye shield.

Thus, preferably the compensation system in accordance with this aspect of the invention is embodied wherein each of the plurality of loads comprises a heating element region on an eye shield and each corresponding PWM channel is for providing the same power density to each heating element region for even heating across the entire eye shield. This even heating embodiment of the invention further preferably comprises a data lookup table of PWM duty cycle values organized according to power setting and battery depletion voltage drop and for use by the code steps to select a compensating duty cycle for application to each PWM to drive each load consistently at the user-determined power setting despite decrease in battery voltage resulting from battery depletion.

Further, preferably, the compensation system in accordance with this aspect of the invention to provide consistent heating in accordance with a custom profile is embodied wherein each of the plurality of loads comprises a heating element region on an eye shield and each corresponding PWM channel is for providing a power density to each heating element region in accordance with the custom heating profile across the eye shield. This custom heating embodiment further comprises a plurality of data lookup tables of PWM duty cycle values, one data lookup table for each different power density specified by the custom heating profile, each data table being organized according to power setting and battery depletion voltage drop and for use by the code steps to select a compensating duty cycle for application to each PWM to drive each load consistently at the corresponding power setting despite decrease in battery voltage resulting from battery depletion.

Each of the aspects of the invention, whether single channel PWM-driven, or multi-channel PWM-driven, provides for consistent power to the load of a portable electronic device, despite charge/ or power, depletion or dissipation of the battery over time in use. Thus, these aspects of the invention provide a consistent feedback to the user who is reinforced and supported in coming to expect that a certain power setting on the device, selected from a series of power settings such as 2 Watts, 4 Watts, 6 Watts, 8 Watts or 10 Watts, will effectively heat the portable device at the desired power level during anticipated weather conditions.

The compensation system of the invention, whether single-channel PWM or multi-channel PWM embodiments of the invention, further preferably comprises a data lookup table of PWM duty cycle values organized according to power setting and battery depletion voltage drop and for use by the code steps to select a compensating duty cycle for application to the PWM to drive the load consistently at the user-determined power setting despite decrease in battery voltage resulting from battery depletion.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

BRIEF DESCRIPTION OF THE DRAWINGS

FIG. 15 is a sample data table of duty cycles to be applied by a PWM to a battery compensation system in accordance with the invention;

FIG. 17 is another sample data table of duty cycles to be applied by a PWM to a battery compensation system in accordance with the invention.

DETAILED DESCRIPTION

Pulse-Width Modulation

Figure 1:
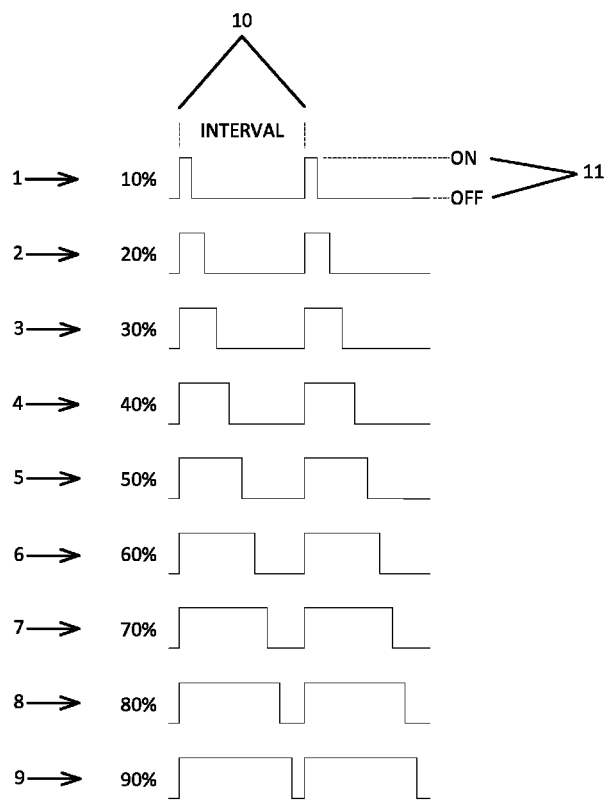
FIG. 1 is a graphic representation of a plurality of electrical signals emanating from a pulse-width modulator (PWM)

Pulse-Width Modulation (PWM) is used mostly in motor speed control applications for varying the speed of a motor. Referring to FIG. 1, PWM is characterized by either an analog or a digital signal generated by a pulse width modulator, such as an analog oscillator, or a digital logic device, which provides varying duty cycles that are a percentage on, for example such as 10%, 20%, 30%, and up to 90% or more, on, and a corresponding percentage off, such as 90%, 80%, 30%, and down to 10% or less, off, all as illustrated by numbers 1-9 on FIG. 1. Dotted lines 10 are used to point out the wavelength of the PWM signal, and dotted lines 11 are used to point out the constant voltage magnitude on (high) condition and the constant voltage magnitude off (low) condition. Thus, for example, where the PWM circuit connected to a 12-volt battery is 40% on and 60% off, one might say that the PWM signal represents a 12-volt PWM circuit at 40% power. Thus, the PWM circuit can run a motor at 40% of its maximum speed, or alternately another percentage of the motor's maximum speed, with a constant voltage source and without adjusting voltage, and this provides the effect of providing a continuous lower voltage by regulating the current delivered to the motor. PWM signals typically have a fixed frequency as is the case with those shown in FIG. 1, and they are typically of a constant full voltage at the full voltage level or a constant no voltage at the low voltage level, though this is not absolutely necessary.

Single-Region, Single-PWM Embodiment

Figure 2:
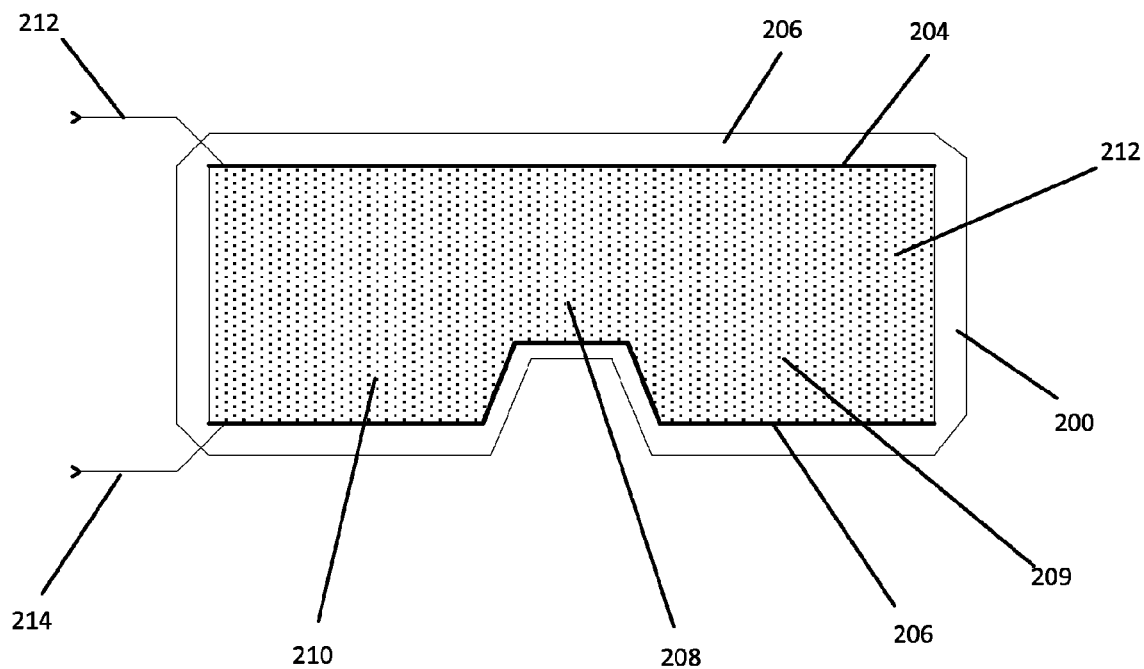
FIG. 2 is a front plan view schematic representation of an irregular-shaped eye shield having a single-region, resistive heating element film heater thereon.

Referring to FIG. 2, there is provided in accordance with part of a first embodiment of the invention an eye shield lens or protective eyewear 200 adapted for at least partially defining an enclosure around a user's eyes and having thereon a single-region resistive transparent conductive film heating member 202. Along an upper edge of the film heating member 202 there is a bus-bar heating element 204 interconnected with a power source (not shown) via a lead wire 212. The film heating member 202 may be comprised of indium-tin oxide (ITO) or other material designed in the form of a resistive element that generates heat when connected to an electrical circuit.

A lower buss-bar heating element 206 is provided along a lower edge of the film heating member 202 and which is interconnected with the power source via another lead wire 214. As is typical with many eye shields, such as in the case of winter sports goggles, the eye shield lens 200 is irregular shaped having two wider similarly shaped square, rectangular, circular or elliptical areas 209, 210, directly anterior of a user's eye during use, and a narrower area 208 above the bridge of the nose of the user during use. Because of the different shapes of the lens 200 at each of these regions, and since the area over the bridge of the nose is smaller than directly in front of the eyes, there would be a tendency for the lens to be hotter over the bridge of the nose since there would be lesser measured electrical resistance in this area.

Figure 5:
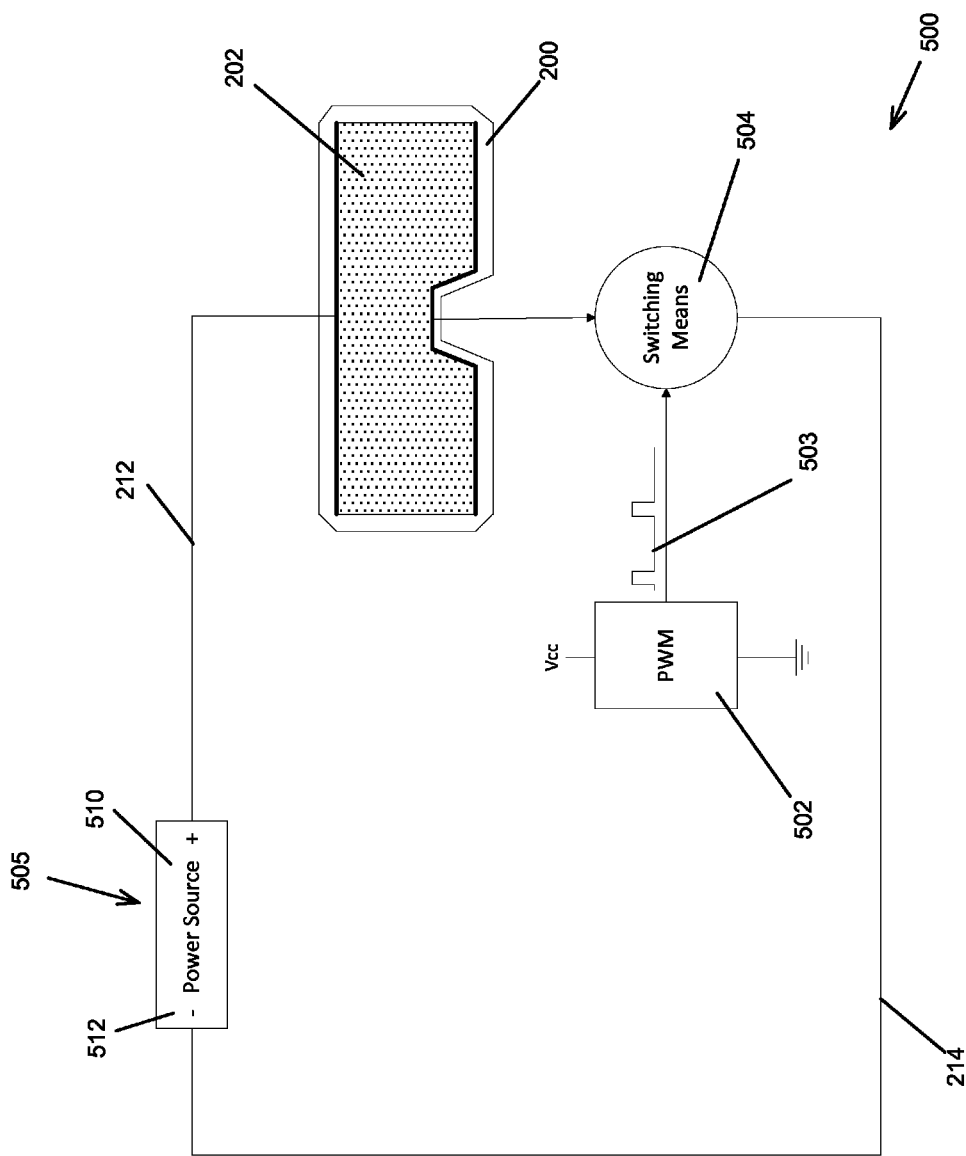
FIG. 5 is a schematic representation of a single-PWM, single-region eye shield fog prevention system in accordance with an aspect of the invention.
Figure 6:
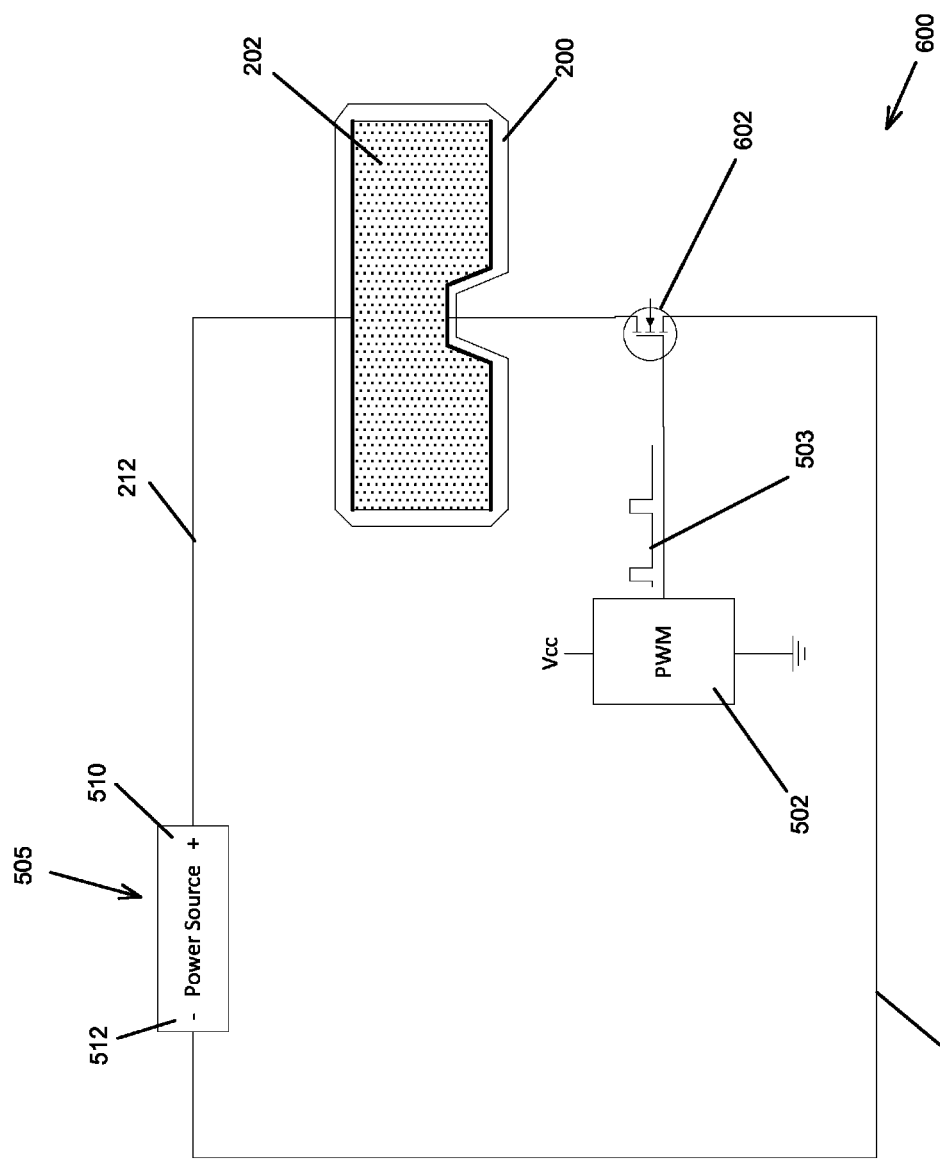
FIG. 6 is a schematic representation of a single-PWM, single-region eye shield fog prevention system in accordance with an aspect of the invention.

As shown in FIG. 5, a first embodiment of the invention is provided as a single-PWM, single-region fog prevention system 500 in accordance with the first aspect of the invention. System 500 comprises a single PWM 502 for generating a constant ratio PWM signal 503, switching means 504, such as preferably a MOSFET switch as shown in FIG. 6, a heating element 202 deposited on a lens 200, and a power source 505 having positive and negative terminals 510, 512. The foregoing elements are interconnected in a circuit via a positive lead wire 212 and a negative lead wire 214. PWM signal 503 controls switching means 504 which controls power to the heating element 202. Since in this embodiment of the invention there is no means of varying input voltage to the PWM 502, the PWM is set to a constant ratio, on to off, that would allow for heating of a single-region heating element 202 on the lens 200 at a constant temperature. Referring to FIG. 6, a single-PWM, single-region fog prevention system 600 is shown comprising a battery power source 505 having positive and negative terminals 510, 512, circuit wires 212, 214, PWM 502 (which generates signal 503), eye shield 200 and heating element 202 which is the same as system 500 except the generic switching means has been replaced with a MOSFET switch 602. While preferably a MOSFET switch is employed with the current invention, other switching means including relays, power transistors or other currently known switches may be used without departing from the true scope and spirit of the invention.

Current Adjustment Means (CAM)

Figure 7:
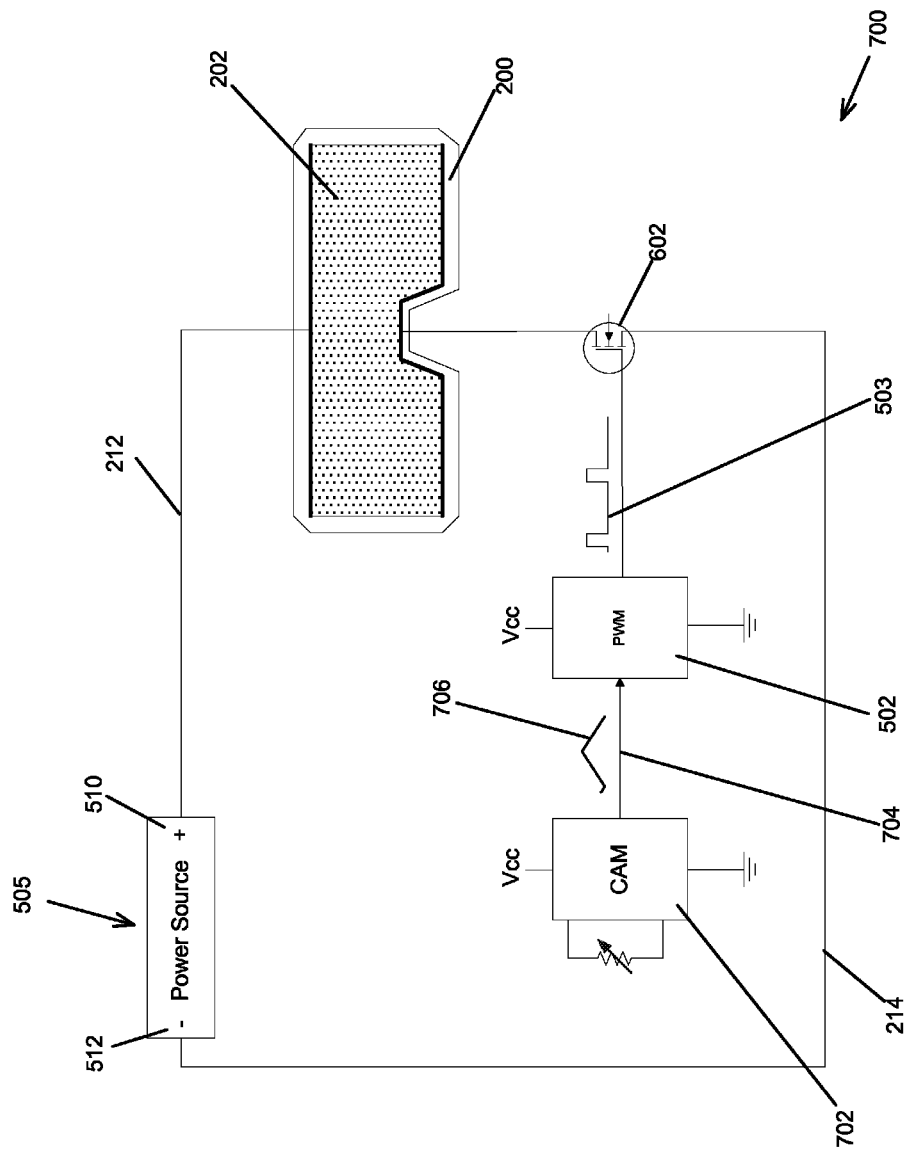
FIG. 7 is a schematic representation of another embodiment of a single-PWM, single-region eye shield fog prevention system in accordance with an aspect of the invention.

Referring now to FIG. 7, a single-PWM, single-region fog prevention system 700 is shown comprising a battery power source 505 having positive and negative terminals 510, 512, circuit wires 212, 214, PWM 502 (which generates signal 503), MOSFET 602, eye shield 200 and heating element 202 which system is the same as system 600 except the system 700 further comprises a current adjustment means (CAM) 702. In this embodiment of the invention, the CAM 702 is shown as a device which comprises a potentiometer and has an internal reference voltage (vref) that is lower than the battery minimum usable voltage and provides an output voltage (input voltage to the PWM), the output voltage from the CAM being some voltage between zero and the reference voltage (vref) based upon the setting of the potentiometer. Responsive to the CAM 702, the PWM 502 produces a corresponding percentage on/off signal that can be varied as a result of output from the CAM. In a preferred system using digital logic, as shown and further described below in connection with FIG. 11, a software control CAM responsive to a MORE (increase) button and responsive to a LESS (decrease) button directly varies the duty cycle of the PWM and thereby varies the amount of current delivered to the heating element 202 without requiring an intermediate voltage reference.

An output line 704 carrying the output voltage of the CAM 702 is operatively connected between the CAM and the PWM 502. The PWM 502 translates the output voltage from the CAM 702 into a signal having a duty cycle corresponding and proportional to the magnitude of the voltage into the PWM. The duty cycle of the PWM's 502 output will therefore vary in relation to the voltage in from the CAM 702 such that a near-zero input voltage from the CAM to the PWM will result in a near-zero percent on/near 100 percent off duty cycle output of the PWM. By contrast, where the voltage from the CAM 702 to the PWM 502 is near the maximum voltage (vref) of the CAM, a resulting near 100 percent on/near-zero percent off duty cycle output of the PWM would result. Further, and accordingly, for each intermediate setting of the CAM 702 between minimum and maximum output voltage to the PWM 502, a corresponding intermediate percentage on/percentage off duty cycle output of the PWM would result. Thus, the CAM 702 enables varied output duty cycles of the PWM 502.

Figure 9:
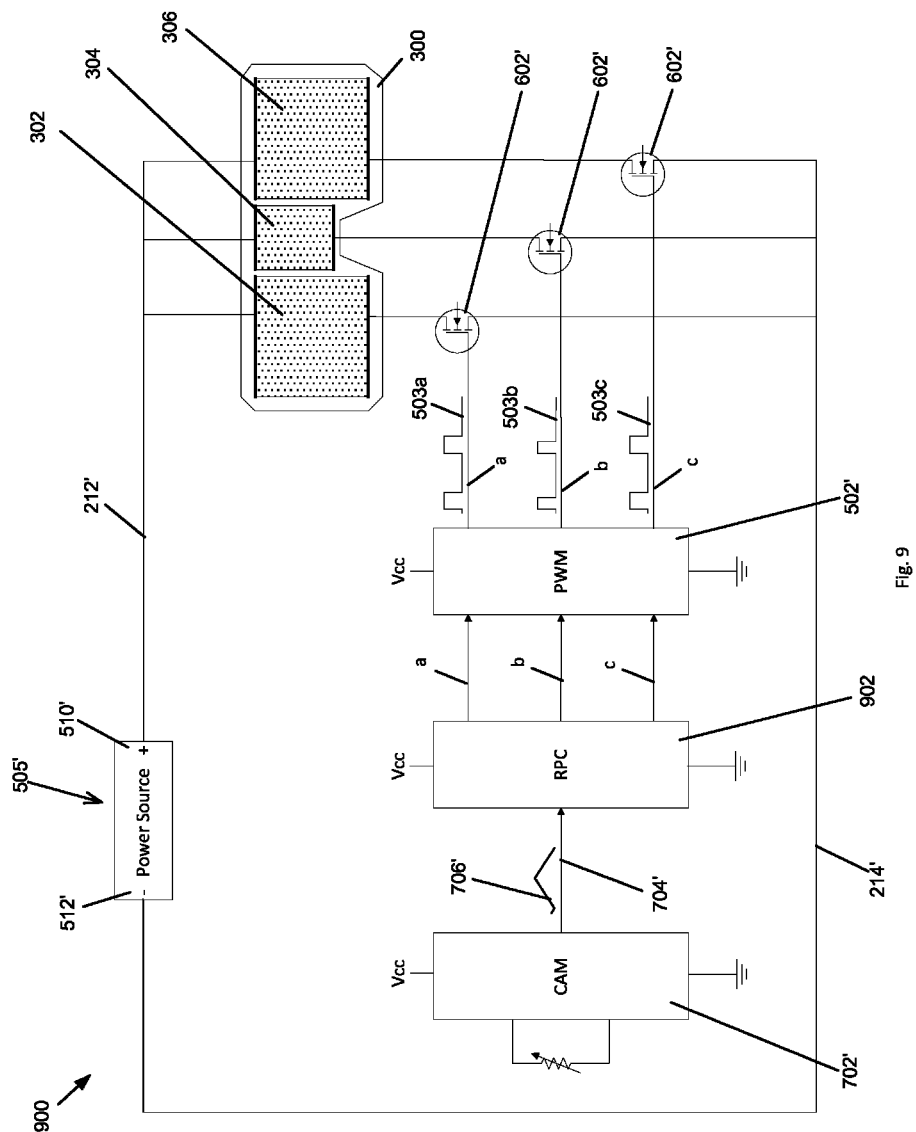
FIG. 9 is a schematic representation of still another embodiment of a multiple-PWM, multiple-region eye shield fog prevention system in accordance with another aspect of the invention.

As further described below, a current adjustment means, such as CAM 702, may also be used with a multiple-region embodiment of the invention as shown in FIG. 9.

Dew Point Calculation and Automation

Figure 8:
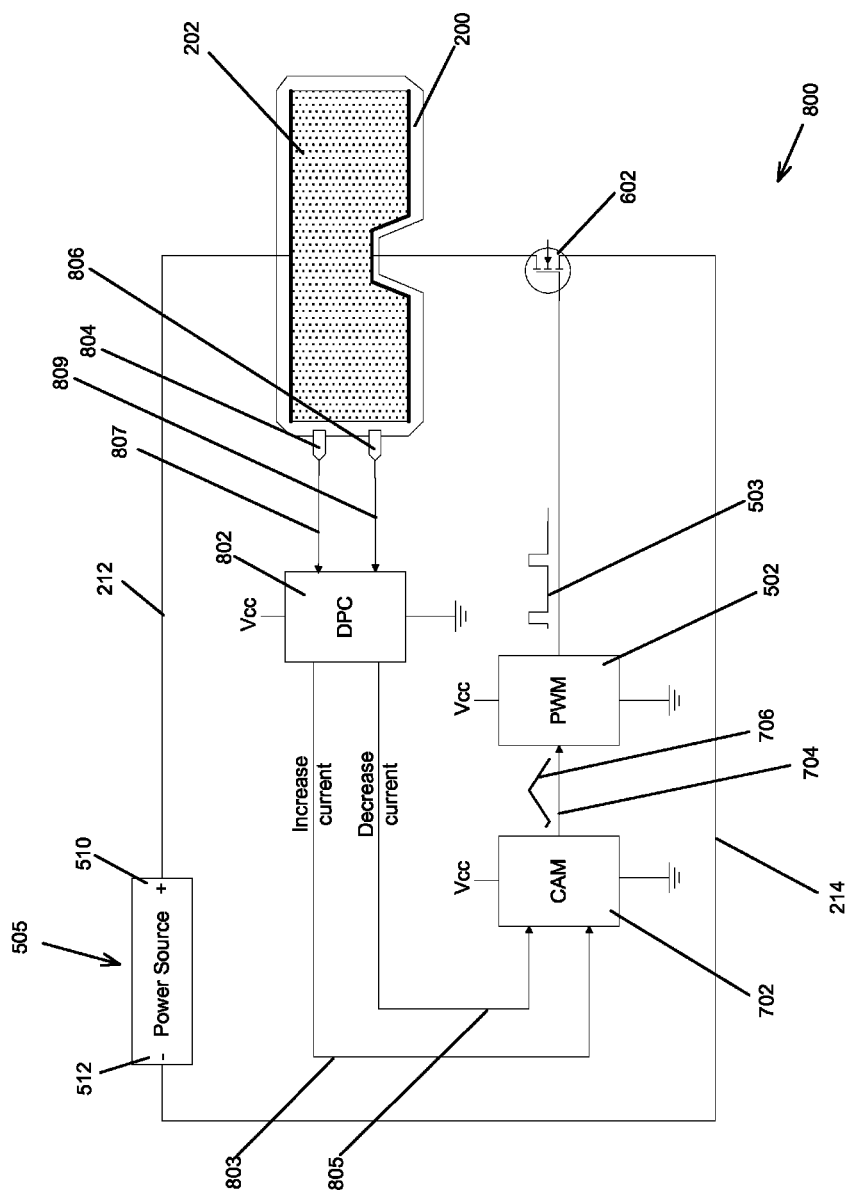
FIG. 8 is a schematic representation of yet another embodiment of an automated single-PWM, single-region eye shield fog prevention system in accordance with another aspect of the invention.

Referring now to FIG. 8, a single-PWM, single-region fog prevention system 800 is shown comprising a power source 505 having positive and negative terminals 510, 512, circuit wires 212, 214, PWM 502 (which generates signal 503), MOSFET 602, eye shield or lens 200 and heating element 202 which system is the same as system 700 except that system 800 further comprises means 802, preferably a microcomputer, for calculating dew point (dew point calculator, or DPC), a temperature sensor 804 and a relative humidity sensor 806 operatively connected to the DPC via signal means 807, 809 and in accordance with another aspect of the invention. This aspect of the invention enables automation of adjustment of the CAM based upon temperature sensor 804 and relative humidity sensor 806 inputs taken from sensing environmental conditions within the space defined between the eye shield 200, near the heating element 202, and the user's eyes.

As shown, the DPC 802 is operatively connected with the CAM 702 via electrical signal means 803 to signal an increase in current and signal means 805 to signal a decrease in current such that the DPC signals the CAM when environmental conditions within the space defined by the eye shield 200 have changed thus requiring an adjustment to the heating element 202 from the system 800. When the system 800 is initially started, the DPC 802 calculates the dew point temperature and compares it to the actual temperature within the space defined by the eye shield 200 and signals the CAM 702 accordingly. If the dew point temperature, as calculated by the DPC 802, is greater than the temperature within a space defined between the eye shield 200 and a user's eyes, then logic within the DPC signals to the CAM 700 to increase the voltage out to the PWM 502, which in turn increases the duty cycle of the PWM output, which in turn increases power to the heating element to increase the temperature of the eye shield 200 and the space between the eye shield and a user's eyes. Thus, subsequent sensory input to the system 800 from the temperature sensor 804, the relative humidity sensor 806, and calculations by the DPC 802, would all reflect not only changing ambient conditions, but temperature changes resulting from the aforementioned increase request from the system 800 as well. Further adjustments to the system 800 via the DPC 802 are made at regular intervals in the following manner: as temperature within the space defined by the eye shield 200 falls below the dew point temperature threshold, the system 800 increases power to the heating element 202 via circuit wires 212, 214, and as temperature within the space defined by the eye shield climbs above the dew point temperature threshold, the system decreases power to the heating element via the circuit wires. The aforementioned operation may employ hysteresis, such as used on a typical thermostat, between the increase and decrease states of the system 800 to avoid unwanted rapid switching.

Multiple-Region, Multiple-PWM Embodiment

Figure 3:
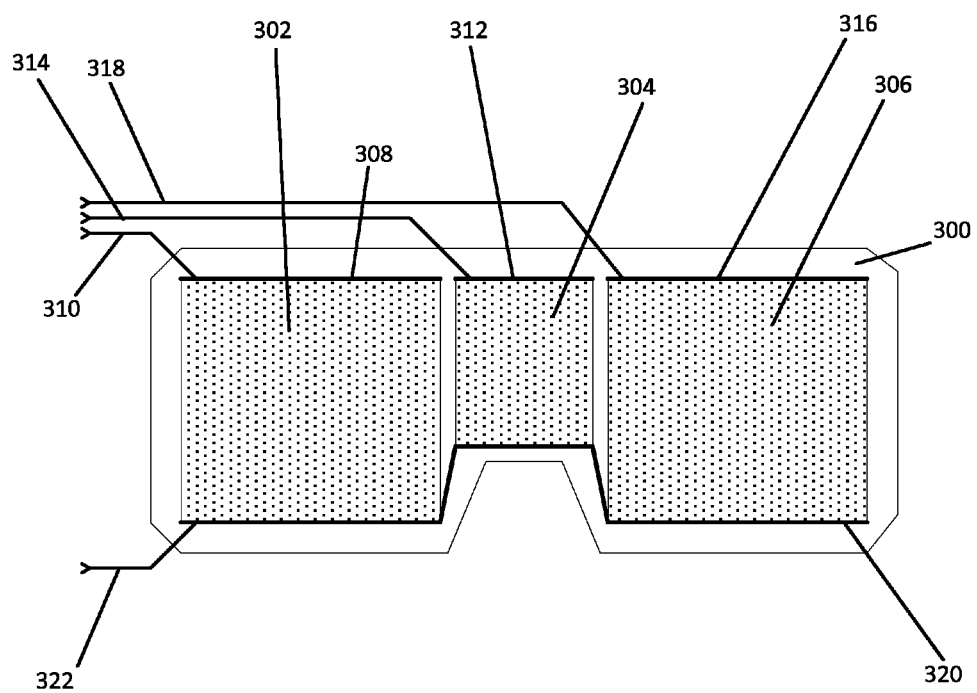
FIG. 3 is a front plan view schematic representation of an irregular-shaped eye shield having a resistive heating element film heater thereon that is divided into a plurality of regions.

Referring to FIG. 3, there is provided in accordance with part of another, second, embodiment of the invention, an eye shield lens or protective eyewear 300 adapted for at least partially defining an enclosure around a user's eyes and having thereon a plurality of regions or zones of resistive film heating elements or members 302, 304, 306. The film heating element 302 located over a user's right eye during use, is connected to the power source (not shown) by a bus-bar 308 positioned along an upper edge of the film and electrically connected between the film and a lead wire 310 leading to a terminal of the power source. The film heating element 304 located centrally of the eye shield lens 300 just above a user's nose during use, is connected to the power source by a bus-bar 312 positioned along an upper edge of the film and electrically connected between the film and a lead wire 314 leading to a terminal of the power source. The film heating element 306, located over a user's left eye during use, is connected to the power source by a bus-bar 316 positioned along an upper edge of the film and electrically connected between the film and a lead wire 318 leading to a terminal of the power source. A buss-bar 320 positioned along the lower edge of each of the film elements 302, 304, 306 interconnects the film elements to the ground terminal of the power source.

As shown, the surface area of the film members 302, 306 is larger than the surface area of the film member 304, such that the resistance of the film member 304 is less than that of the other film members. Accordingly, in order to have even heating across the entire lens 300, less current should be applied to the film member 304 than the other film members. Or, alternatively, the divisions between the film members would allow independent heating of one or more of the film members, more or less, than the other film members.

Figure 4:
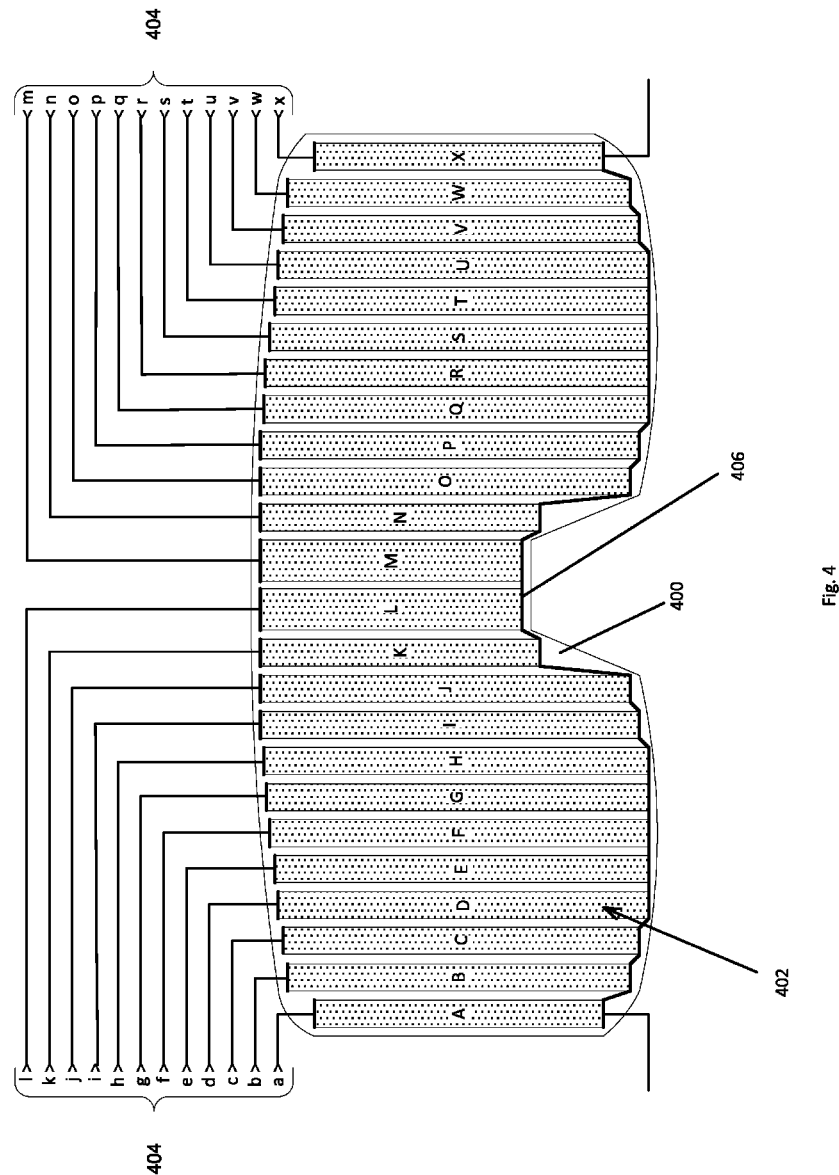
FIG. 4 is a front plan view schematic representation of an irregular-shaped eye shield having a resistive heating element film heater thereon that is divided into a plurality of regions.

Referring to FIG. 4, an eye shield lens 400 is provided in accordance with the second embodiment of the invention. The eye shield 400 is adapted for at least partially defining an enclosure in front of the user's eyes and has deposited thereon a plurality (24 are shown in FIG. 4) of resistive heating film zones or regions 402 A-X. It will be appreciated that the resistive heating film may be divided into larger or smaller regions than shown without departing from the true scope and spirit of the invention. Each resistive film region 402 A-X is connected to a terminal of a power source via lead wires and discrete buss-bars 404 *a-x*. A single buss-bar 406, located along a lower edge of each resistive film region 402 A-X interconnects each of the lower ends of film regions to a ground terminal of the power source.

The resistive film regions of the fog prevention system of the present invention are preferably deposited on the inner surface of an eye shield 200, 300, 400 with a process known as ion sputtering on a polycarbonate lens, but spray coating and other methods and materials known in the art may be used without departing from the true scope and spirit of the invention. The buss-bars are deposited on the lens 200, 300, 400 by stamping, adhesive backing, or in the case of a conductive silver epoxy buss-bar, it may be applied to a polycarbonate substrate. In the case of a dive mask, while attachment of the resistive film and buss-bars to the inner glass surface of the mask may be employed, a preferred alternative would be to apply these to an inner polycarbonate substrate within the mask. The methods and systems of application of the resistive film heaters and the buss-bars to various substrates are known in the art. Each buss-bar and its corresponding resistive film region are overlapped on edge portions of each so that they conduct electricity to and from the power source as is known in the art.

CAM and DPC in a Multiple-Region Embodiment

Figure 10:
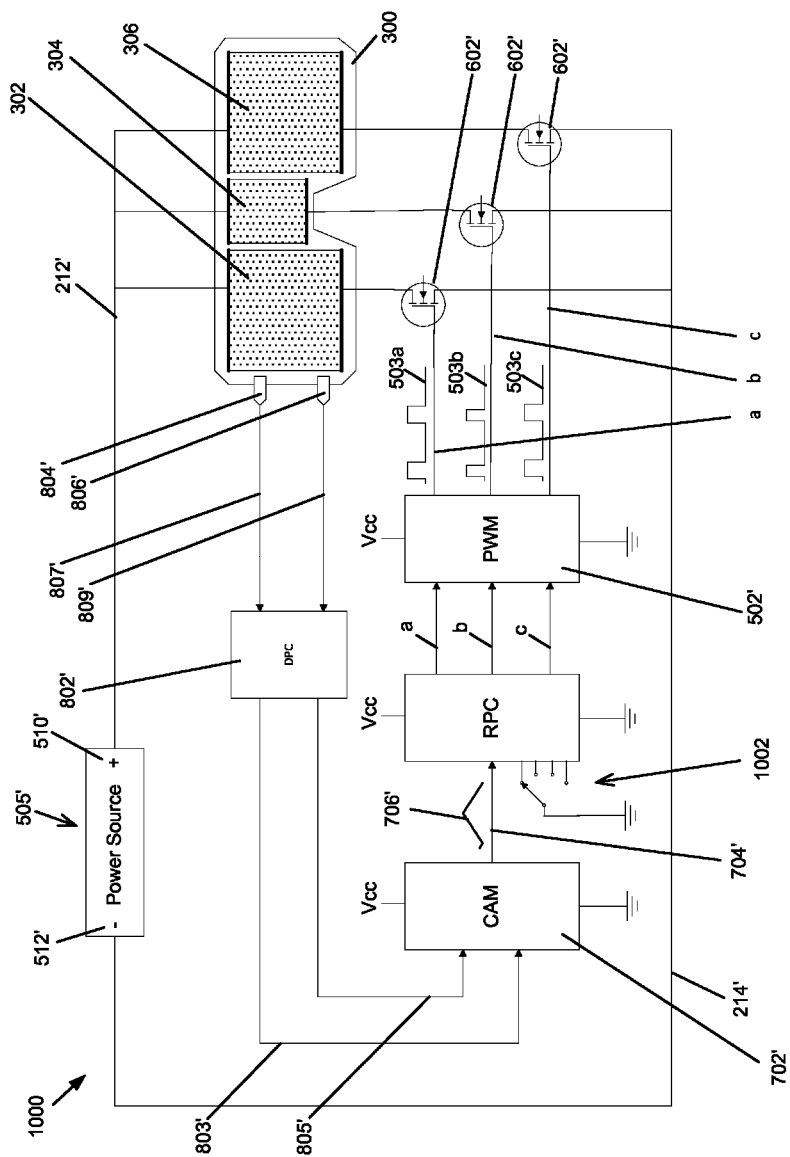
FIG. 10 is a schematic representation of another embodiment of an automated multiple-PWM, multiple-region eye shield fog prevention system in accordance with yet another aspect of the invention.

The larger number of resistive film regions 302, 304, 306 in the multiple-region embodiment of the invention shown in FIG. 3, and alternatively the larger number of regions 402 A-X in the multiple-region embodiment of the invention shown in FIG. 4, enables more even heating of a wider variety of shapes and sizes of eye shields 300, or alternatively 400, and requires a correspondingly larger number of Pulse-Width Modulators (PWMs), or PWM channels, in a multiple-region, multiple-PWM eye shield fog prevention system as shown in FIGS. 9 and 10. Thus, it will be appreciated that, while a three-channel PWM system is shown in FIGS. 9 and 10, fewer or more channels may be provided to accommodate a like number of resistive heating element regions by using an appropriate number PWM channels to accommodate such a plurality of heating element regions.

As shown in FIGS. 9 and 10, a current adjustment means (CAM) may be employed with a multiple-region embodiment of the invention, and as shown in FIG. 10, a dew point calculation means (DPC) may also be incorporated into a multiple-region embodiment of the invention to enable automated adjustment of each region as described above. In the case of the CAM, the single output voltage of the CAM is received by a region profile control means (RPC) as further described below and used to adjust the input voltage to each of the multiple PWMs in that embodiment to allow varying of the current out of the PWM based upon user adjustment of a selector or to enable automation as further described below. The DPC of the multiple-region embodiment of the invention functions the same way as described above for the DPC in a single-region embodiment of the invention.

Balancing Profiles and Custom Profiles

Referring now to FIG. 9, a multiple-PWM, multiple-region fog prevention system 900 is shown comprising a power source 505' having positive and negative terminals 510', 512', circuit wires 212', 214', a multiple-channel PWM 502' which is shown generating signals 503a, 503b and 503c on channels a, b and c, respectively, a CAM 702', a plurality of MOSFETs 602', one MOSFET for each channel of the multiple-channel PWM, an eye shield or lens 300 and heating element regions 302, 304, 306, which system is similar to the single-PWM systems described above, except that system 900 further comprises a region profile controller 902 primarily for balancing power delivered to different-sized and shaped resistive heating film regions (302, 304, 306, or alternatively, 402 A-X), on the eye shield 300 or 400, respectively.

Differently shaped eye shield lenses 300, 400 would require corresponding region profiles that reflect the shape of the lens and its individual regions such that the electrical characteristics of each region are appropriately weighted so that each region is assured the proper amount of power to keep it in balance with other regions. Thus a region profile is tied to the shape of a region (and the resulting electrical resistivity of that region) and the overall shape of the goggle. If one were to change the shape of a lens, then a different profile would be required for that lens.

Calculating the Resistance of Regions

Each of the regions 302, 304 and 306 have a calculated total electrical resistance (Rt) determined by a formula which considers the type of resistive coating used, and the area of the region where: Rt is the total resistance of the region in ohms, Ri is the resistance per square inch of the resistive thin film in ohms, H is the height of the region in inches and W is the width of the region in inches. Rt may be calculated using the following formula:

$$Rt = \frac{Ri * H}{W}$$

For example, considering the regions 302 and 306, given Ri is 10 ohms, H is 3 inches, and W is 3 inches. The total resistance (Rt) for each region 302 and 306 may be calculated as (10×3)/3 which equals 10 ohms. Now considering region 304, given an Ri of 10 ohms, H being 2 inches, and W being 1.6 inches, the total resistance (Rt) of the region 304 may be calculated as (10×1.6)/2 which equals 8 ohms. Thus, for a given voltage, due to a lower total resistance in 304 than in regions 302, 306, more power would be consumed in region 304 than in regions 302 and 306 causing a hot spot in region 304 as further verified below.

Calculating the Power Density of Regions

Each region 302, 304, 306 has a calculated Power Density (Pd) determined by a formula which considers the effective voltage (E) applied to the region, the resistance per square inch (Ri) of the resistive thin film in ohms, and the width (W) of the region in inches. Pd may be calculated using the following formula:

$$Pd = \frac{E^2}{Ri * W^2}$$

For example, considering regions 302 and 306, given an operating voltage of 10 volts for each region, Pd would equal $10^2/(10\times3^2)$ which equals 1.11 watts per square inch. Considering region 304, given the same operating voltage of 10 volts, region 304 Pd would equal $10^2/(10\times2^2)$ which equals 2.5 watts per square inch. These calculations show that, given an equal effective voltage for all regions, the center region 304 will be hotter than the outside region 302 and 306.

Determining Region Profile Proportional Control

Given the aforementioned determined hot spot over the nose of the user, proportional balancing of the regions is desirable. Such balancing requires a determination of an appropriate voltage level for region 304 which will provide the same power level output as regions 302 and 306 when powering regions 302 and 306 at 10 volts. Previously, according to the formula, $$\frac{E^2}{Ri * W^2} = 1.11 \ (Pd \text{ same as } 302)$$

and solving for E, $$E = \sqrt{Ri * W^2 * Pd}$$

and plugging in known values, E is equal to $$\sqrt{10 * 2^2 * 1.11}$$ which is equal to 6.66 volts.

Therefore, based on the width and height of the same material used in regions 302 and 306, to produce an equivalent power density, region 304 will need 0.666 times (or 66.6%) of the voltage applied to regions 302 and 304. This result is confirmed by re-calculating the power density (Pd) for region 304 as $6.66^2/(10\times2^2)$ which equals 1.11 watts per square inch.

Applying these calculations back to the reference output voltage produced by the CAM 702' on channels a and c, delivered to regions 302 and 306 respectively, will also require reduction of the reference output voltage on channel b by 66.6% compared to the values applied to channels a and c. In the case of analog circuitry this proportional control may be accomplished by use of a resistor network as will be appreciated by those of ordinary skill in the art. In the case of a digital implementation the values will be retrieved from a data table and the resulting power levels will be calculated and applied directly to the PWM channels using a microcomputer or equivalent digital circuitry as will be apparent to those of ordinary skill in the art.

Region Profile Matched to Shape or Region

Accordingly, it should be understood that when a larger region or regions receive 100% of the applied effective voltage, smaller regions should receive a proportionally smaller percentage of the applied effective voltage to balance the power density of all of the regions. While a specific example for a particularly shaped goggle has been provided, it will be appreciated that differently-shaped lens regions will require similar calculation and balancing profile determination. In the case of curved edge, or irregularly shaped regions, determination of region areas may require the application of known mathematical methods to determine the region area for use in the above-described calculations.

Balanced and Custom Profiles

The results in the foregoing example disclose a balancing profile. More precisely, these results yield the analog or digital proportional input voltages needed to power differing size regions on a specific goggle to the same power densities.

Region Custom Profile Switch and Automation

Referring to FIG. 10, a multiple-PWM, multiple-region fog prevention system 1000 similar to system 900 is shown comprising a power source 505' having positive and negative terminals 510', 512', circuit wires 212', 214', a multiple-channel PWM 502' which is shown generating signals 503$a$, 503$b$ and 503$c$ on channels a, b and c, respectively, a CAM 702', a plurality of MOSFETs 602', one MOSFET for each channel of the multiple-channel PWM, an eye shield or lens 300 and heating element regions 302, 304, 306. System 1000 differs from system 900 in that in system 1000 the RCP 902 further comprises a user-selectable region profile control switch 1002 which enables a user to select a balanced profile or one of several custom profiles for customized power delivery as further described below to the different-sized and shaped resistive heating film regions (302, 304, 306, or alternatively 402 A-X) on the eye shield 300 or 400, respectively.

A custom profile may be used to enable predetermined proportional input voltages to a particular resistive film region, or regions, necessary to achieve a desired power density pattern allowing one or more regions 302, 304, 306, or alternatively 402 A-X, to intentionally become hotter or cooler than other regions for specific intended purposes. Together with the DPC 802' and sensors 804', 806', the CAM 702' provides overall automatic variability between all the way cool to all the way hot for each of the regions 302, 304, 306, or alternatively regions 402 A-X, and it is the job of the RPC 902' cognizant of the profile to know how much power to apply proportionally to each of the regions in accordance with the overall adjustment. For example for a given dew point calculation, the CAM 702' may be set to a 50% overall power application or duty cycle, the RPC will put out a 50% adjustment for the largest region 302, 304, 306 (or alternatively 402 A-X) and a proportionally smaller output for smaller regions in accordance with a particular predetermined profile.

Examples of custom profiles may involve a profile for a snow boarder that may require added heat to one side of a goggle lens to prevent fogging or to reduce icing of that side depending upon which foot the rider usually leads downhill, or as another example, a particular lens or goggle shape and configuration may require added heating at the edges of the goggle to prevent fogging or icing. Alternatively, further it would be desirable to provide custom settings for particular weather conditions, such as a rainy day, a snowy day, a sunny day, or different depths and water temperatures for a dive mask, etc. Custom profiling may be user-selectable with the custom profile switch 1002.

The multiple-PWM, multiple-region fog prevention system 1000 shown in FIG. 10 also further comprises means for calculating dew point 802' (also known as the dew point calculator, or DPC), a temperature sensor 804' and a relative humidity sensor 806' operatively connected to the DPC via signal means 807', 809' for automated control of the system 1000. The DPC 802' and sensors 804', 806' are for the same purposes and function in the same way as the DPC 802 and sensors 804, 806 shown and described above in connection with the first embodiment of the invention, except the signals from the DPC 802' are used by the CAM and RPC to provide master controls for a plurality of signal lines a, b, c to the PWM 502'.

From the foregoing it can be seen that many of the aspects of the invention, such as dew point calculation, automation and current adjusting means may be employed to either of the first or second embodiments of the invention, whereas the RPC is primarily adapted for the second embodiment of the invention employing a plurality of regions on the eye shield.

System Overview

While preferably the PWMs of either embodiment of the invention, and associated functions such as dew point calculation, profile table lookup, variable current adjustment mechanism, switching means, and the like, may be preferably accomplished with a microcomputer, any of these functions may be performed with other technology, such as a programmable logic array (PLA), a state machine, analog circuitry or other digital logic, without departing from the true scope and spirit of the invention.

Figure 11:
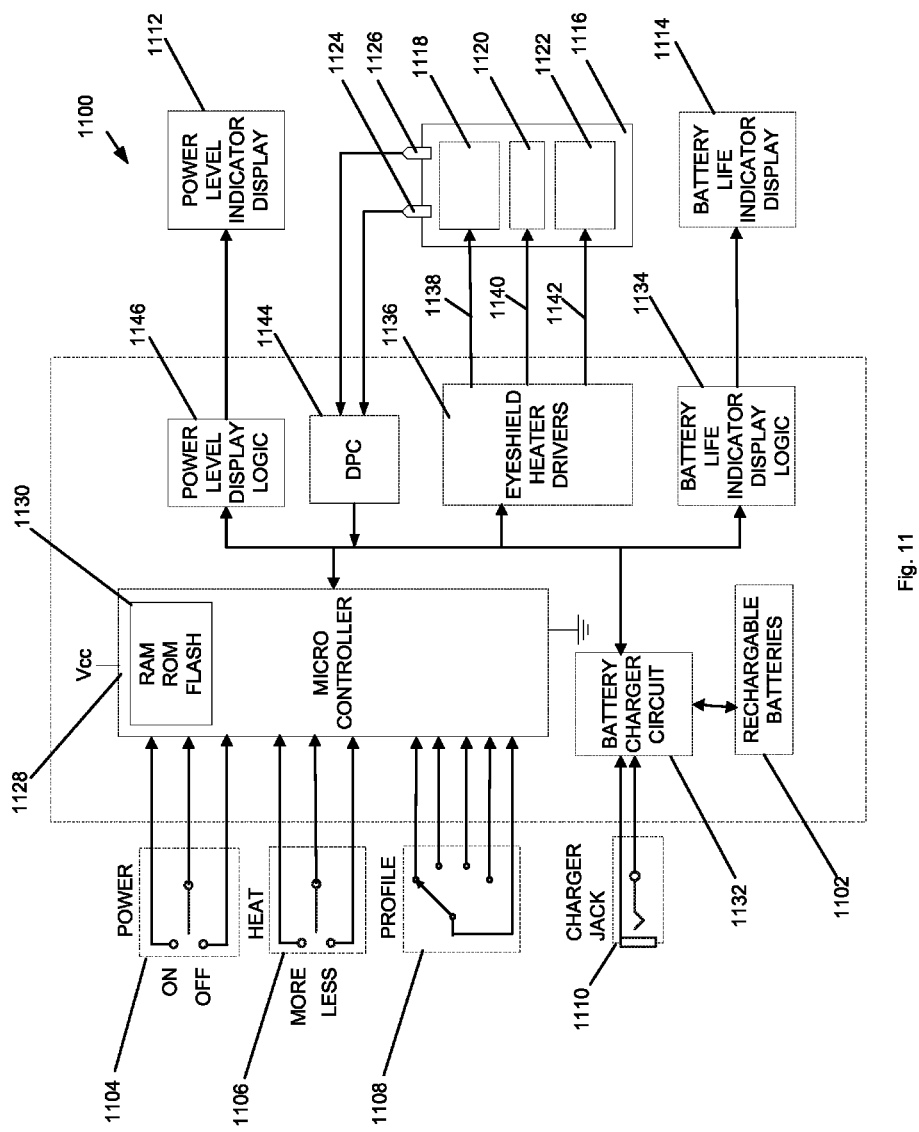
FIG. 11 is a schematic representation of a micro-computer controlled embodiment of an automated multiple-PWM, multiple-region eye shield fog prevention system also including a charger.

Referring to FIG. 11, there is provided a preferred embodiment of a digital version of a multiple-channel PWM, multiple-region fog prevention system 1100. System 1100 comprises a power source, such as rechargeable batteries 1102, an on/off switch 1104, a heat control switch 1106, a profile selector 1108 and a charger jack 1110. Charger jack 1110 may comprise a mini-USB charger jack or other suitable charging system as known in the art. System 1100 further comprises a power level indicator display 1112 preferably comprising a plurality of LEDs configured as a bar graph to indicate a selected power level and a battery life indicator display 1114 preferably comprising a plurality of LEDs configured as a bar graph to indicate remaining battery life. System 1100 further comprises an eye shield 1116 having deposited thereon a plurality of thin film heating elements 1118, 1120, 1122. The eye shield 1116 is adapted for defining at least a partial enclosure in front of a user's eyes. A temperature sensor 1124 and a relative humidity sensor 1126 are positioned within the partial enclosure defined by the eye shield 1116 for aiding with calculation of dew point temperature.

The system 1100 further preferably comprises a low-power microcontroller 1128 preferably further comprising PWM logic, other programmable logic and some combination of RAM/ROM/FLASH Memory 1130 as is known in the art of microelectronics. The microcomputer controller 1128 is operatively connected to a battery charger circuit 1132. The battery charger circuit 1132 is connected to the battery charger jack 1110 and rechargeable batteries 1102. The battery charger circuit 1132 is primarily responsible for maintaining the rechargeable batteries 1102, including routing a charge from the charger jack 1110 to the rechargeable batteries when required and turning off, disconnecting the charger from the batteries when they have been fully charged and reporting battery level to the microcontroller 1128. The system 1100 further comprises battery life indicator display logic 1134 such that when the microcontroller 1128 receives battery level information from the battery charger circuit as previously described, the microcontroller may signal the battery life indicator display logic upon user request or otherwise. The battery life indicator display logic 1134 converts the signal received from the microcontroller 1128 into the logic necessary to drive the battery life indicator display 1114. The battery life indicator display logic 1134 may include a latch to hold the latest value on the display, relieving the microcomputer to attend to other tasks.

The system 1100 further comprises an eye shield heater driver 1136 comprising a plurality of driver channels 1138, 1140, 1142, each channel corresponding to a thin film heating element region or zone, such as regions 1118, 1120, 1122, respectively. The primary responsibility of the microcontroller 1128 is to keep the heater driver 1136 and related channels 1138, 1140, 1142 operating at an optimal and preferably balanced level to eliminate and prevent fogging while conserving battery life. The microcontroller 1128 may operate in manual heat control or automatic heat control modes. In the manual heat control mode, responsive to an input from the more or less heat switch 1106, the microcontroller 1128 adjusts power to the eye-shield heater driver 1136 according to a predetermined profile contained in microcontroller memory 1130 and which controls the duty cycle signal on each individual PWM channel in a manner consistent with the size, shape and electrical resistivity of each associated heating element 1118, 1120, 1122 to provide power density balancing.

In the situation where some other custom profile, other than power density balancing, is desired, responsive to input from profile selector switch 1108, the system 1100 may engage a custom profile, also stored in microcontroller memory 1130, resulting in application of a custom power density profile to the heater driver 1136 resulting in a desired portion of the eye shield 1116 receiving more power than another portion.

The system 1100 further comprises a dew point calculator (DPC) 1144 which calculates dew point temperature from temperature sensor 1124 and relative humidity sensor 1126. During automatic mode balancing of heating levels of the system 1100, the system adjusts the heat to the regions in accordance with a calculated dew point from the DPC 1144. When the system 1100 is initially started, the DPC 1144 calculates the dew point temperature and compares it to the actual temperature within the space defined by the eye shield 1116 and signals the microcontroller 1128 accordingly. If the dew point temperature, as calculated by the DPC 1144, is greater than the temperature within the space defined between the eye shield 1116 and a user's eyes, then logic within the microcontroller signals to the eye shield heater driver 1136 to increase the duty cycle of the PWM channels in accordance with the profile in effect to increase the temperature of the eye shield 1116 and the space between the eye shield and a user's eyes. Thus, subsequent sensory input to the DPC 1144 from the temperature sensor 1124, the relative humidity sensor 1126, and calculations by the microcontroller 1128, would all reflect not only changing ambient conditions, but temperature changes resulting from the aforementioned increase request from the system 1100 as well. Further adjustments to the system 1100 via the DPC 1144 are made by the microcontroller 1128 at regular intervals in the following manner: as temperature within the space defined by the eye shield 1116 falls below the dew point temperature threshold, the system 1100 increases power to the heating elements 1118, 1120, 1122 via PWM channels 1138, 1140, 1142, and as temperature within the space defined by the eye shield climbs above the dew point temperature threshold, the system decreases power to the heating elements via the PWM channels. The aforementioned operation may employ hysteresis, such as used on a typical thermostat, between the increase and decrease states of the system 1100 to avoid unwanted rapid switching.

In both the manual and automatic operation modes of the system 1100, it is preferable for the user to be apprised of the power level being supplied to the heating elements of the system. This is especially useful in the manual mode when the user may set the power at a predetermined level in accordance with visual feedback from the power level display. In response to manual changes from the more/less heat switch 1106, and/or at regular intervals, the microcontroller 1128 determines from memory 1130 the current operating power level being supplied to the heater driver 1136 and sends a power level signal to the power level display logic 1146, which in turn converts the signal received from the microcontroller 1128 into the logic necessary to drive the power level indicator display 1112. The power level indicator display logic 1146 may include a latch to hold the latest value on the display, relieving the microcomputer to attend to other tasks.

Prior Voltage Regulation System

Figure 12:
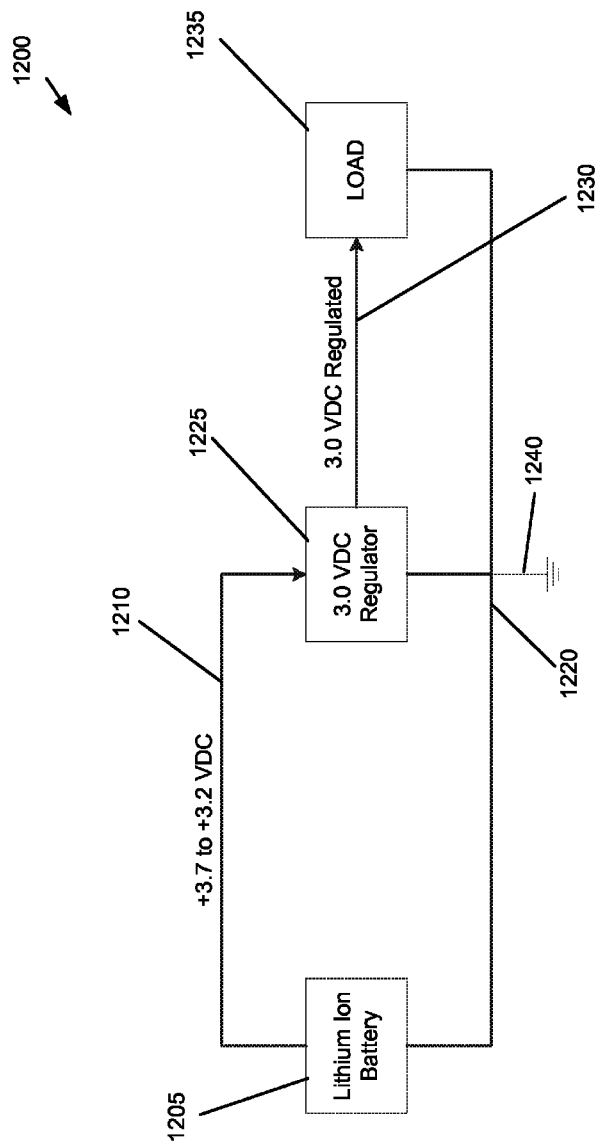
FIG. 12 is a block diagram of a prior system for regulating battery voltage that otherwise depletes over time in use.

Referring now to FIG. 12, a block diagram of a battery regulation system is illustrated for maintaining a constant regulated voltage to a hand-held electronic device, such as a cell phone (represented by load 1235), including a lithium-ion battery 1205, a positive circuit wire 1210 carrying 3.7 to 3.2 Volts DC, which is depleting with battery discharge over time in use as specified, to a voltage regulator 1225. The voltage regulator 1225 is set to supply a regulated, constant 3.0 Volts DC via line 1230 as specified to the load 1235. A typical voltage regulator supplies voltage at the desired output level only when the actual supply voltage from the battery is somewhat greater than the desired output voltage. Thus, for example, where the desired output voltage is to be 3.0 Volts DC, the battery voltage would need to be at least 3.2 Volts DC for the voltage regulator to produce the desired 3.0 Volts DC. The circuit back to the negative terminal of the battery 1205 is completed with circuit line 1220, and the system is grounded at 1240. Such a system is known to be important to provide constant voltage necessary to efficient functioning of cell phones.

Battery Compensation System Using PWM

Unlike the aforementioned battery regulation system 1200 shown and described above, a battery compensation system using PWM differs in that it does not maintain a constant voltage until the battery is discharged, but rather it varies the PWM cycle to maintain constant power to the load despite the voltage drop until the battery is discharged and no longer able to maintain that power level.

Figure 13:
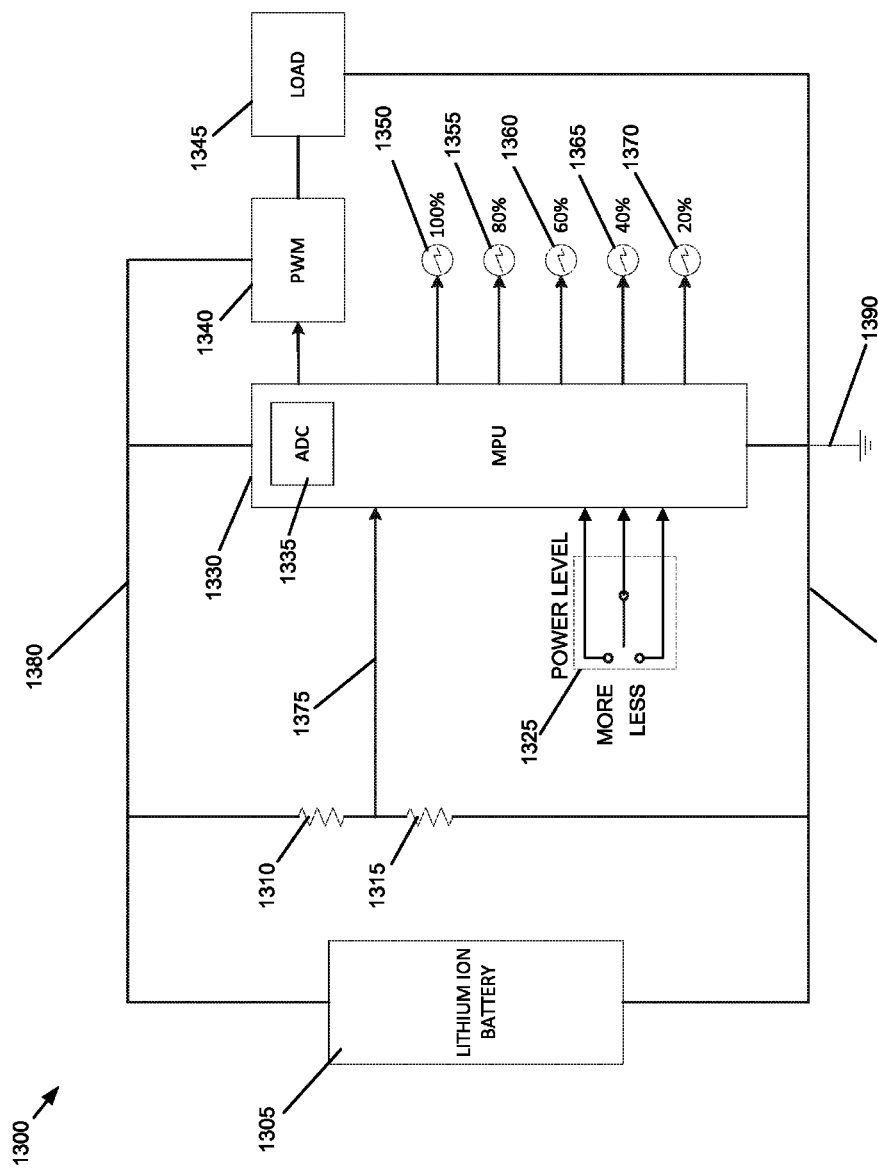
FIG. 13 is a block diagram of an alternate embodiment of a battery compensation system in accordance with an aspect of the invention.

Thus, referring now to FIG. 13, a battery compensation system 1300 using pulse-width modulation (PWM) 1340 is shown comprising a battery 1305, preferably a lithium-ion battery, having positive parallel circuit lines 1380 leading to a voltage divider circuit 1310, 1315 for proportionally adjusting the voltage to a measurable range, an analog to digital converter 1335 for receiving the output from the voltage divider and converting it into a digital voltage value, a microprocessing unit (MPU) 1330 and a single-channel pulse-width modulator (PWM) 1340. Preferably, the voltage divider circuit 1310, 1315 comprises two resistors 1310, 1315 in series between positive and negative terminals of the battery 1305 for proportionally adjusting the voltage to a measurable range, the voltage divider circuit preferably having a tap between the two resistors (shown as the intersection of lines between the two resistors 1310, 1315) adapted to provide the proportional voltage measurement to an I/O pin on the analog-to-digital converter 1335. Preferably, the user-determined, or provided, power setting comprises a power level setting set by a dial, a knob, or a push button system 1325, together with some form of visual feedback to the user (e.g., 1612 of FIG. 16) to further enable selection of the setting.

The PWM 1340 drives the load 1345, which represents a portable electronic device, or elements of a portable electronic device, such as for example heating elements on an anti-fog ski goggle, a heated diving mask, a heated medical or technical eye shield, or the like. Alternatively, the load 1345 may represent a heater on a portable electronic device such as a hand-held GPS unit, a cell phone, a radio, an electronic tablet, a reader, or other portable computer or the like, to be driven by the PWM circuitry and battery of the device. A power level selector 1325 is provided with more and less controller for allowing user selection of a desired power setting, such as 20%, 40%, 60%, 80% 100%, corresponding to, for example, 2 Watts, 4 Watts, 6 Watts, 8 Watts and 10 Watts respectively 1350, 1355, 1360, 1365, 1370 respectively, for power to drive a heater (e.g., heating element 202 of FIG. 5) on the powered electronic device (e.g., an anti-fog goggle). The MPU 1330 is one of several possible means for receiving voltage input and user-determined power setting input for determining a compensating duty cycle 1350, 1355, 1360, 1365, 1370 for application to the PWM 1340 to drive the load consistently at the user-determined power setting despite decrease in voltage from the battery 1305 resulting from battery depletion.

Figure 14:
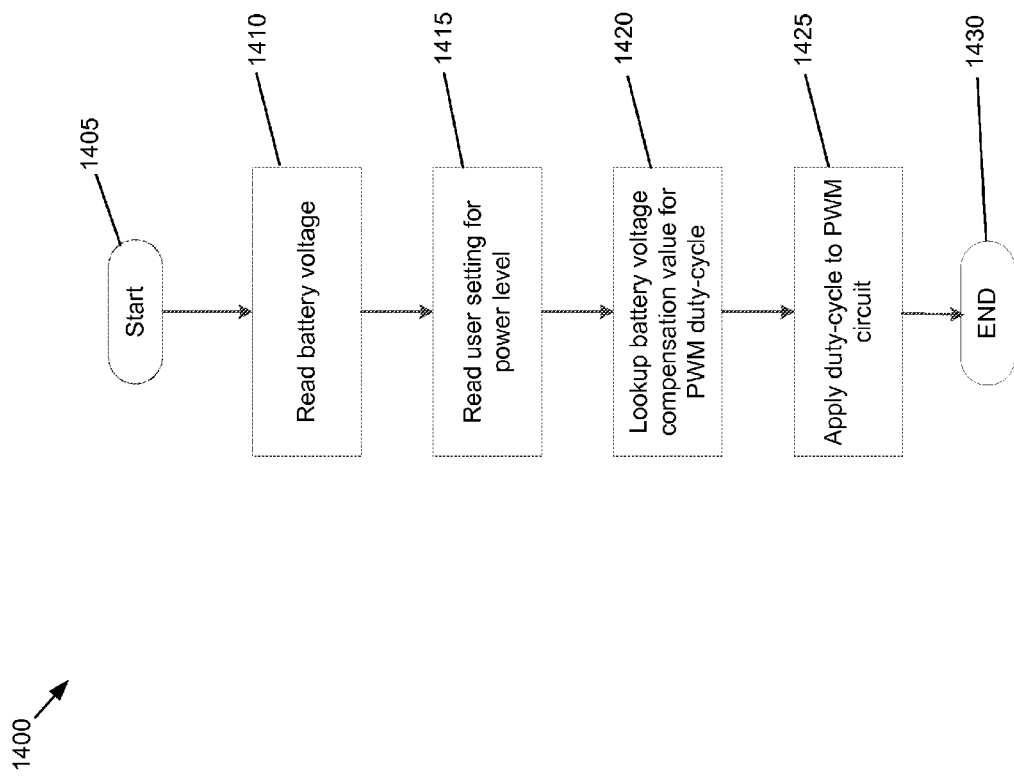
FIG. 14 is a flow diagram of software steps for performing the functions of a battery compensation system in accordance with the present invention.

Referring now also to FIG. 14, the MPU 1330 is capable of executing software code steps 1400 as set forth in the flow chart, to determine a compensating duty cycle 1350, 1355, 1360, 1365, 1370 for application by the software to the PWM 1340 to drive the load 1345 consistently at the user-determined power setting despite decrease in battery voltage resulting from depletion of the battery 1305. For this embodiment of the invention, preferably the MPU 1330 is battery-powered, and a readily-available microprocessing unit having on-board analog-to-digital conversion means 1335 may be used for the present invention.

The software steps as shown at 1405 for operation of the invention comprise, after starting at 1405, reading of the battery voltage 1410, reading the user setting for power level 1415, looking up the battery voltage compensation value for a PWM duty cycle 1420 to be applied to the PWM circuit 1425. The process ends at 1430, and the steps 1400 are repeated frequently as needed to maintain compensated power in accordance with the invention during operation of the system. While the portable electronic device 1345 (e.g., 200 of FIG. 5) is powered on, the compensation system of the invention may be operated continuously, or it may be controlled with an on/off switch to toggle between battery conservation mode and battery compensation mode. As indicated by line 1430 for as long as the device power is on and the battery is sufficiently charged and capable of supplying the power necessary to power the device in battery compensation mode. While battery conservation mode will use less battery power, battery compensation mode in accordance with the invention may be employed when extra battery power is available to compensate for a drop in voltage resulting from battery depletion by increasing the duty cycle 1350, 1355, 1360, 1365, 1370 to be applied to the PWM 1340 to overcome what would otherwise be a drop in power associated with the depleted battery 1305.

Still further, as shown in FIGS. 14 and 15, determination of a compensating duty cycle 1350, 1355, 1360, 1365, 1370 may comprise a data lookup table 1500 of PWM duty cycle values organized according to power setting (shown in Watts across the top of the table 1500) and battery depletion voltage drop (shown in the left-hand column of FIG. 15) and for use by the code steps 1410, 1415, 1420, 1425 run by the microprocessor to select a compensating duty cycle for application to the PWM to drive the load 1345 consistently at the user-determined power setting despite a decrease in voltage from the battery 1305 resulting from battery depletion. This embodiment of the invention preferably comprises a lookup table 1500 stored in microprocessor memory (e.g., 1630 of FIG. 16) which, as is true of software data table controls in general, provides generally faster operation and is easier to code than using floating-point calculations, though it will be appreciated that either may be used to implement the invention in accordance with its true spirit and scope. Further, while conceivably a discrete logic circuit could be used to perform the functions of the compensation system of the invention, such would likely be unduly expensive to implement and no more effective than the software and data table lookup functions that are preferred for the invention.

The data lookup table 1500 shown in FIG. 15 is organized by user heater level setting (shown in Watts across the top of the table 1500) and actual heater power for a given battery voltage ranging from 8.4 Volts DC (assuming two lithium-ion batteries of 3.7 Volts DC each in series) depleted down to 6.8 Volts DC (shown in the left-hand column of the table 1500). Thus, for example, when the battery 1305 is at full power (that is there has been no depletion of battery charge yet), and 2 Watts of total power has been selected by a user, 11.3 on cycles (out of 100.0 total cycles) will need to be on. As can be seen from the FIG. 15, the number of duty cycles increases as shown as a greater number of Watts is specified by the user, and a larger number of duty cycles is required to compensate for increasingly depleted charge in the battery. Thus for example, 86.5 duty cycles (that is PWW will switch the power on 86.5 cycles for every 100 cycles—or in other words the PWM controls transmission of power to allow power to the load 86.5 cycles out of a hundred, or 86.5 on and 13.5 off). Thus, as can be seen the number of duty cycles required increases as the battery depletes further and the higher the power level selected by the user. While the example data table 1500 is based upon a system using two lithium-ion batteries of 3.7 Volts DC each in series, the invention is not limited to a two-battery, or otherwise plural-battery, system, and the battery compensation system of the invention may be used with a single battery with an appropriately adjusted data table, or calculations as the case may be. Further, while the number of duty cycles is represented as an integer with a decimal portion, these numbers may be rounded to the nearest integer in an actual PWM implementation.

In an alternate embodiment, the software steps 1410, 1415, 1420, 1425 themselves may be used to calculate a compensating duty cycle 1350, 1355, 1360, 1365, 1370 for application to the PWM 1340 to drive the load 1345 consistently at the user-determined power setting despite decrease in voltage from the battery 1305 resulting from battery depletion. The formula for determining the compensating duty cycle 1350, 1355, 1360, 1365, 1370 for this embodiment of the invention, which is the same formula used to determine data table 1500 duty cycle values (from user input power settings—represented by the Watts settings across the top of table 1500—and measured voltage) used in the table is as follows:

$$\text{Duty Cycle} = \frac{\text{Desired Power} * \text{Load Resistance}}{(\text{Battery Voltage})^2} * 100$$

The compensation system 1300 in accordance with the invention enables maintenance of a user-selected and/or desired power setting to drive the load 1345 to consistently heat a portable device (e.g., goggle lens 200 of FIG. 5), such as anti-fog goggles or a hand-held GPS, radio or phone, despite partial depletion of a device battery 1305, as long as there is sufficient battery charge to maintain the system-compensated power output. Thus, as the voltage from the battery 1305 drops resulting from battery depletion from use over time, the system 1300 compensates by increasing the duty cycle 1350, 1355, 1360, 1365, 1370 of the PWM 1340 driver for the device 1345.

Figure 16:
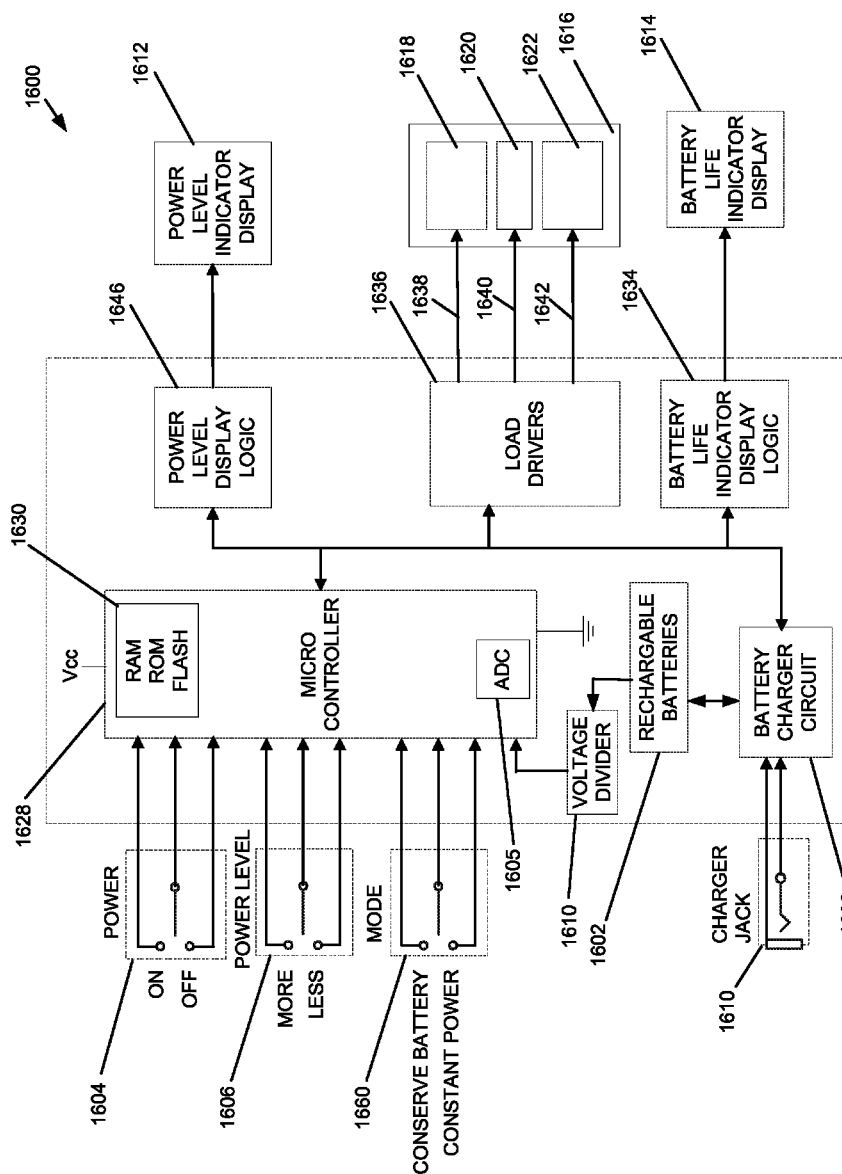
FIG. 16 is a block diagram of an alternate embodiment of a battery compensation system adapted for a multi-load device.

Referring now to FIG. 16, there is shown a compensation system 1600 adapted for use preferably in heating a plurality of devices, for example a plurality of loads 1618, 1620, 1622 of a portable electronic device 1616. The plurality of loads 1618, 1620, 1622 represent a portable electronic device, elements of a portable electronic device, or a plurality of such devices, such as heating elements on an anti-fog ski goggle, a heated diving mask, a heated medical or technical eye shield, or the like. Alternatively, the load 1345 may represent a heater or other appropriately PWM driven element on a portable electronic device such as a hand-held GPS unit, a cell phone, a radio, an electronic tablet, a reader, or other portable computer or the like, to be powered by the PWM circuitry and battery of the device. The example compensation system 1600 comprises a power source, such as rechargeable batteries 1602, an on/off switch 1604, a power level control 1606 and a charger jack 1610. Charger jack 1610 may comprise a mini-USB charger jack or other suitable charging system as known in the art. System 1600 further comprises a power level indicator display 1612 preferably comprising a plurality of LEDs configured as a bar graph to indicate a selected power level and a battery life indicator display 1614 preferably comprising a plurality of LEDs configured as a bar graph to indicate remaining battery life. System 1600 further comprises a portable electronic device 1616 having illustrated therewith a plurality of loads 1618, 1620, 1622.

The system 1600 further preferably comprises a low-power microcontroller 1628 preferably further comprising PWM logic, other programmable logic and some combination of RAM/ROM/FLASH Memory 1630 as is known in the art of microelectronics. The microcomputer controller 1628 is operatively connected to a battery charger circuit 1632. The battery charger circuit 1632 is connected to the battery charger jack 1610 and rechargeable batteries 1602. The battery charger circuit 1632 is primarily responsible for maintaining the rechargeable batteries 1602, including routing a charge from the charger jack 1610 to the rechargeable batteries when required and disconnecting the charger from the batteries when they have been fully charged and reporting battery level to the microcontroller 1628. The system 1600 further comprises battery life indicator display logic 1634 such that when the microcontroller 1628 receives battery level information from the battery charger circuit as previously described, the microcontroller may signal the battery life indicator display logic upon user request or otherwise. The battery life indicator display logic 1634 converts the signal received from the microcontroller 1628 into the logic necessary to drive the battery life indicator display 1614. The battery life indicator display logic 1634 may include a latch to hold the latest value on the display, relieving the microcomputer to attend to other tasks.

The system 1600 further comprises drivers 1636 comprising a plurality of driver channels 1638, 1640, 1642, each channel corresponding to a load, such as loads 1618, 1620, 1622, respectively. Preferably, MOSFET for system 1600 is contained in the drivers 1636. The primary responsibility of the microcontroller 1628 is to keep the driver 1636 and related channels 1638, 1640, 1642 operating at an optimal and preferably balanced level while conserving battery life. Responsive to an input from the power level control 1606, the microcontroller 1628 adjusts power to the device driver 1636 according to a predetermined profile contained in microcontroller memory 1630 and which controls the duty cycle signal on each individual PWM channel in a manner consistent with the size, shape and electrical resistivity of each associated load 1618, 1620, 1622 to provide power density balancing.

In the situation where some other custom profile, other than power density balancing, is desired, the system 1600 may engage a custom profile, which may be stored in microcontroller memory 1630, resulting in application of a custom power level profile to the driver 1636 resulting in a desired portion of the portable electronic device 1616 receiving more or less power than another portion.

The system 1600 using pulse-width modulation (PWM) (contained in the microcontroller 1628 comprises a voltage divider circuit 1610 for proportionally adjusting the voltage to a measurable range, and an analog to digital converter (ADC) 1605 preferably contained in the microcontroller 1628 for receiving the output from the voltage divider and converting it into a digital voltage value. Preferably, the voltage divider circuit 1610 comprises two precision resistors in series (as described above in connection with FIG. 13) between positive and negative terminals of a battery or batteries 1602 for proportionally adjusting the voltage to a measurable range, the voltage divider circuit preferably having a tap between the two resistors adapted to provide the proportional voltage measurement to an I/O pin on microcontroller 1628 containing the analog-to-digital converter 1605. Preferably, the user-determined, or provided, power setting comprises a power level setting set by a dial, a knob, or a push button system (e.g., 1606), together with some form of visual feedback to the user (e.g., 1612) to further enable selection of the setting.

As part of system 1600, it is preferable for the user to be apprised of the power level being supplied to the load elements of the system. Thus, a user may select a desired power level in accordance with visual feedback from the power level display 1612. In response to manual changes from the power level control 1606, and/or at regular intervals, the microcontroller 1628 determines from memory 1630 the current operating power level being supplied to the driver 1636 and sends a power level signal to the power level display logic 1646, which in turn converts the signal received from the microcontroller 1628 into the logic necessary to drive the power level indicator display 1612. The power level indicator display logic 1646 may include a latch to hold the latest value on the display, relieving the microcomputer to attend to other tasks.

Referring now to FIG. 17, there is shown an alternate data lookup table 1700 stored in microprocessor memory 1630 for allowing software determination of an applied duty cycle corresponding to a custom power level profile, for example for each load of a plurality of different loads, in a portable electronic device, for example when less than full power to the device may be desirable. The data lookup table 1700 shown in FIG. 17 is organized by user heater level setting (shown in Watts across the top of the table 1700) and actual heater power for a given battery voltage ranging from 8.4 Volts DC (assuming two lithium-ion batteries of 3.7 Volts DC each connected in series) depleted down to 6.8 Volts DC (shown in the left-hand column of the table 1700). Thus, for example, when the battery 1602 is at full power (that is there has been no depletion of battery charge yet), and 1.5 Watts of total power has been selected by a user, 8.5 on cycles (out of 100.0 total cycles) will need to be on. As can be seen from the FIG. 17, the number of duty cycles increases as shown as a greater number of Watts is specified by the user, and a larger number of duty cycles is required to compensate for increasingly depleted charge in the battery. Thus for example, 64.9 duty cycles (that is PWW will switch the power on 64.9 cycles for every 100 cycles—or in other words the PWM controls transmission of power to allow power to the load 64.9 cycles out of a hundred, or 64.9 on and 35.1 off). Thus, as can be seen the number of duty cycles required increases as the battery depletes further and the higher the power level selected by the user. While the example data table 1700 is based upon a system using two lithium-ion batteries of 3.7 Volts DC each in series, the invention is not limited to a two-battery, or otherwise plural-battery, system, and the battery compensation system of the invention may be used with a single battery with an appropriately adjusted data table, or calculations as the case may be. Further, while the number of duty cycles is represented as an integer with a decimal portion, these numbers may be rounded to the nearest integer in an actual PWM implementation.

The table 1700 may be part of a more comprehensive data table and still fall within the true scope and spirit of the invention, however it is contemplated that the system 1600 will ascertain the battery voltage and the user-determined power level input, and determine the appropriate duty cycle according to those inputs and in harmony with either an even power level profile, or alternatively a custom power level profile, such as would the be case for example in an evenly-heated eye shield device or a custom-heated eye shield device described previously for example in connection with FIG. 11.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. Thus, by way of example, it will be appreciated that while the system 1100 discloses a preferred way of accomplishing the purposes of invention, it will be appreciated by those of ordinary skill in the art that other combinations of microcontrollers and/or microcontrollers may be used to accomplish the purposes hereof without departing from the true scope and spirit of the invention. The appended claims are therefore intended to cover all such changes and modifications as fall within the true spirit and scope of the invention.

The invention claimed is:

1. A compensation system adapted for use with a battery-powered, PWM-driven portable electronic device to enable consistent power to the device load despite battery voltage drop resulting from battery depletion, comprising:
   a voltage divider circuit for proportionally adjusting the voltage to a measurable range;
   an analog to digital converter for receiving the output from the voltage divider and converting it into a digital voltage value; and
   means for receiving digital voltage input and user-determined power setting input for determining a compensating duty cycle for application to the PWM to drive the load consistently at the user-determined power setting despite decrease in battery voltage resulting from battery depletion.

2. The compensation system of claim 1, further comprising mode switching means for user selection of battery conservation mode or consistent power output mode.

3. The compensation system of claim 1, wherein the system is adapted for use with a lithium-ion battery-powered, PWM-driven portable electronic device.

4. The compensation system of claim 1, wherein the system is adapted for used for heating with an anti-fog eye shield.

5. The compensation system of claim 1, wherein said means for receiving voltage input and user-determined power setting input for determining compensating duty cycle further comprises software code steps executed by a microprocessing unit.

6. The compensation system of claim 5, further comprising a data lookup table of PWM duty cycle values organized according to power setting and battery depletion voltage drop and for use by the code steps to select a compensating duty cycle for application to the PWM to drive the load consistently at the user-determined power setting despite decrease in battery voltage resulting from battery depletion.

7. The compensation system of claim 5, further comprising software steps to calculate a compensating duty cycle for application to the PWM to drive the load consistently at the user-determined power setting despite decrease in battery voltage resulting from battery depletion.

8. The compensation system of claim 6, further comprising a metal-oxide-semiconductor field-effect transistor switching means responsive to the pulse-width modulator.

9. The compensation system of claim 6, further comprising current adjustment means operatively connected to the pulse-width modulator for varying duty cycle of the power source via the pulse-width modulator in turn varying the mount of current delivered to the load.

10. The compensation system of claim 1, wherein the system is adapted for use for heating with an anti-fog eye shield.

11. A compensation system adapted for use with a battery-powered, PWM-driven portable electronic device to enable consistent power to the device load despite battery voltage drop resulting from battery depletion, comprising:
   a voltage divider circuit further comprising two precision resistors in series between positive and negative terminals of the battery for proportionally adjusting the voltage to a measurable range and having a tap between the two resistors adapted to provide the proportional voltage measurement to an I/O pin on an analog-to-digital converter;
   an analog-to-digital converter for receiving the output from the voltage divider and converting it into a digital voltage value; and
   a microprocessing unit for running software code steps for receiving digital voltage input and user-determined power setting input for determining a compensating duty cycle for application by the software to the PWM to drive the load consistently at the user-determined power setting despite decrease in battery voltage resulting from battery depletion.

12. The compensation system of claim 11, further comprising a data lookup table of PWM duty cycle values organized according to power setting and battery depletion voltage drop and for use by the code steps to select a compensating duty cycle for application to the PWM to drive the load consistently at the user-determined power setting despite decrease in battery voltage resulting from battery depletion.

13. The compensation system of claim 11, further comprising mode switching means for user selection of battery conservation mode or consistent power output mode.

14. The compensation system of claim 11, wherein the system is adapted for use with a lithium-ion battery-powered, PWM-driven portable electronic device.

15. A compensation system adapted for use with a battery-powered, multi-channel PWM-driven portable electronic device having a plurality of loads corresponding to each PWM channel to enable consistent power to each of the loads of the device despite battery voltage drop resulting from battery depletion, comprising:
   a voltage divider circuit for proportionally adjusting the voltage to a measurable range;
   an analog to digital converter for receiving the output from the voltage divider and converting it into a digital voltage value; and
   a microprocessing unit for running software code steps for receiving digital voltage input and user-determined power setting input for each load for determining a compensating duty cycle for application by the software to each PWM channel to drive each corresponding load consistently at the user-determined power setting despite decrease in battery voltage resulting from battery depletion.

16. The compensation system of claim 15, wherein each of the plurality of loads comprises a heating element region on an eye shield and each corresponding PWM channel is for providing the same power density to each heating element region for even heating across the entire eye shield, and further comprising a data lookup table of PWM duty cycle values organized according to power setting and battery depletion voltage drop and for use by the code steps to select a compensating duty cycle for application to each PWM to drive each load consistently at the user-determined power setting despite decrease in battery voltage resulting from battery depletion.

17. The compensation system of claim 15, wherein each of the plurality of loads comprises a heating element region on an eye shield and each corresponding PWM channel is for providing a power density to each heating element region in accordance with a custom heating profile across the eye shield, and further comprising a plurality of data lookup tables of PWM duty cycle values, one data lookup table for each different power density specified by the custom heating profile, each data table being organized according to power setting and battery depletion voltage drop and for use by the code steps to select a compensating duty cycle for application to each PWM to drive each load consistently at the corresponding power setting despite decrease in battery voltage resulting from battery depletion.

* * * * *